United States Patent
Imamura et al.

(10) Patent No.: US 8,592,428 B2
(45) Date of Patent: Nov. 26, 2013

(54) ACETYL PYRROLIDINYL INDOLE DERIVATIVE

(75) Inventors: Hideaki Imamura, Ryugasaki (JP); Takuya Suga, Tsukuba (JP); Hiroyuki Takahashi, Tsukuba (JP); Hideki Jona, Moriya (JP); Etsuko Hirose, Tsuchiura (JP); Norikazu Ohtake, Tsukuba (JP)

(73) Assignee: MSD K. K., Tokyo (JP)

( * ) Notice: Subject to any disclaimer, the term of this patent is extended or adjusted under 35 U.S.C. 154(b) by 79 days.

(21) Appl. No.: 13/058,626

(22) PCT Filed: Aug. 3, 2009

(86) PCT No.: PCT/JP2009/064073
§ 371 (c)(1),
(2), (4) Date: Jun. 7, 2011

(87) PCT Pub. No.: WO2010/018800
PCT Pub. Date: Feb. 18, 2010

(65) Prior Publication Data
US 2012/0108817 A1    May 3, 2012

(30) Foreign Application Priority Data

Aug. 15, 2008 (JP) ................. 2008-209153

(51) Int. Cl.
*A61K 31/497* (2006.01)

(52) U.S. Cl.
USPC ...................... 514/255.05; 544/405

(58) Field of Classification Search
USPC ....................................... 544/405
See application file for complete search history.

(56) References Cited

U.S. PATENT DOCUMENTS

| | | |
|---|---|---|
| 2006/0167053 A1 | 7/2006 | Iino et al. |
| 2006/0258701 A1 | 11/2006 | Mitsuya et al. |
| 2008/0070928 A1 | 3/2008 | Nonoshita et al. |
| 2008/0090799 A1 | 4/2008 | Hashimoto et al. |
| 2008/0125429 A1 | 5/2008 | Hashimoto et al. |
| 2009/0018056 A1 | 1/2009 | Iino et al. |
| 2009/0118304 A1 | 5/2009 | Takahashi et al. |
| 2010/0041660 A1 | 2/2010 | Mitsuya et al. |

FOREIGN PATENT DOCUMENTS

| | | |
|---|---|---|
| WO | 2005/063738 | 7/2005 |
| WO | 2007/037534 | 4/2007 |
| WO | 2010/107610 | 9/2010 |

OTHER PUBLICATIONS

Vionnet et al., "Nonsense mutation in the glucokinase gene causes early-onset non-insulin-dependent diabetes mellitus", Nature (1992), vol. 356, pp. 721-722.
Glaser et al., "Familial hyperinsulinism caused by an activating glucokinase mutation", New England J. of Medicine (1998), vol. 338, pp. 226-230.
Ferre et al., "Correction of diabetic alterations by glucokinase", PNAS (1996), vol. 93, pp. 7225-7230.
Grupe et al., "Transgenic knockouts reveal a critical requirement for pancreatic beta cell glucokinase . . . ", Cell (1995), vol. 83, pp. 69-78.
Garfinkel et al., "Computer modeling identifies glucokinase as glucose sensor of pancreatic beta cells", Am. J. Physiol. (1984), vol. 247, pp. R527-R536.
Klapars et al., "Enantioselective Pd-catalyzed alpha-arylation of N-Boc-Pyrrolidine: . . . ", J. Org. Chem. (2008), vol. 73, pp. 4986-4993.
Int'l Search Report of PCT/JP2009/064073, dated Sep. 29, 2009.
Int'l Preliminary Report on Patentability of PCT/JP2009/064073, dated Feb. 15, 2011.

*Primary Examiner* — Brian McDowell
(74) *Attorney, Agent, or Firm* — Anna L. Cocuzzo; Catherine D. Fitch

(57) ABSTRACT

The present invention relates to compounds, which are useful for treatment and/or prevention of diabetes mellitus, diabetes mellitus complications or obesity, since the compounds have glucokinase-activating effects, and are presented in Formula (I): wherein $R^1$ represents a lower alkylsulfonyl group; $R^2$ represents a hydrogen atom; $R^{20}$ represents, e.g., a hydrogen atom; m represents an integer of from 1 to 3; and n represents zero or 1, or relates to a pharmaceutically acceptable salts thereof.

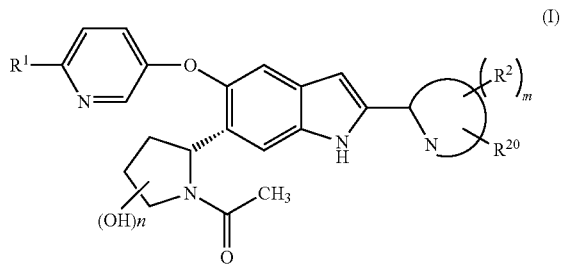

18 Claims, No Drawings

ACETYL PYRROLIDINYL INDOLE DERIVATIVE

TECHNICAL FIELD

The present invention relates to a glucokinase activator comprising an acetyl pyrrolidinyl indole derivative as the active ingredient thereof. Further, it relates to a novel acetyl pyrrolidinyl indole derivatives.

BACKGROUND ART

Glucokinase (GK) (ATP: D-hexose 6-phosphotransferaze, EC 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) except glucokinase is saturated at a glucose concentration of at most 1 mM, but Km of glucokinase to glucose is 8 mM and is near to a physiological blood-glucose level. Therefore, in accordance with the blood-glucose level change from a normal blood-glucose level (5 mM) to an increased blood-glucose level after meals (10 to 15 mM), intercellular glucose metabolism is accelerated via glucokinase.

Since ten years ago, a hypothesis that glucokinase may act as a glucose sensor in pancreas beta cells and liver has been proposed (for example, see Garfinkel D, et al., "Computer modeling identifies glucokinase as glucose sensor of pancreatic beta-cells", American Journal Physiology, Vol. 247 (3Pt2), 1984, pp. 527-536). A result of recent glucokinase gene-manipulated mice has confirmed that glucokinase actually plays an important role in systemic glucose homeostasis. Mice in which the glucokinase gene was disrupted die soon after their birth (for example, see Grupe A. et al., "Transgenic knockouts reveal a critical requirement for pancreatic beta cell glucokinase in maintaining glucose homeostasis", Cell, Vol. 83, 1995, pp. 69-78), but on the other hand, normal or diabetic mice in which glucokinase was excessively expressed have a lowered blood-glucose level (for example, see Ferre T. et al., "Correction of diabetic alterations by glucokinase", Proceedings of the National Academy of Sciences of the U.S.A., Vol. 93, 1996, pp. 7225-7230).

With the increase in glucose concentration therein, the reaction of pancreas beta cells and that of liver cells are both toward the reduction in a blood-glucose level, though differing from each other. Pancreas beta cells come to secrete more insulin, and liver takes up sugar to store it as glycogen therein and simultaneously reduces glucose release.

To that effect, the change in the enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood-glucose level increase (for example, see Vionnet N. et al., "Nonsense mutation in the glucokinase gene causes early-onset non-insulin-dependent diabetes mellitus", Nature Genetics, Vol. 356, 1992, pp. 721-722). On the other hand, a pedigree having mutation of increasing glucokinase activity has been found, and those of the family line show low blood-glucose level symptoms (for example, Glaser B. et al., "Familial hyperinsulinism caused by an activating glucokinase mutation", New England Journal Medicine, Vol. 338, 1998, pp. 226-230).

From these, glucokinase acts as a glucose sensor and plays an important role in glucose homeostasis also in humans. On the other hand, blood-glucose level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, and therefore it may be useful as a remedy for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neutrons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VMH, a glucose-mediated mechanism is anticipated like the insulin secretion in pancreas beta cells. Accordingly, there may be a possibility that a substance for glucokinase activation in VMH, in addition to liver and pancreas beta cells, may be effective not only for blood-glucose level correction but also for solution of obesity that is problematic in many type-II diabetes patients.

From the above description, a compound having a glucokinase-activating effect is useful for remedies and/or preventives for diabetes, or for remedies and/or preventives for chronic complications of diabetes such as retinopathy, nephropathy, neurosis, ischemic cardiopathy, arteriosclerosis, and further for remedies and/or preventives for obesity.

Compounds that have glucokinase-activating effects and an indole skeleton, including a compound of Formula (I) shown below, are disclosed in WO 2007/037534.

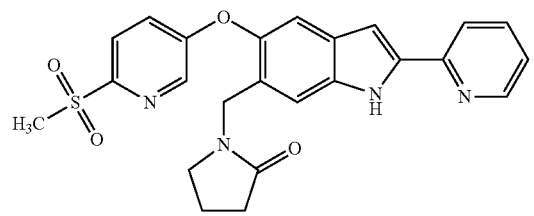 [SMILES: CS(=O)(=O)c1ccc(Oc2cc3cc(-c4ccccn4)[nH]c3cc2CN2CCCC2=O)cn1]

It is desirable for use as pharmaceutical preparations that compounds with glucokinase-activating effects have high solubility in water as well as adequate glucokinase-activating effects.

However, although WO 2007/037534 discloses that the above-mentioned compounds having an indole skeleton or the like have adequate glucokinase-activating effects, it does not mention the solubility of the compounds having an indole skeleton in water at all.

DISCLOSURE OF THE INVENTION

The present invention provides compounds of the following formula (I), and pharmaceutically acceptable salts, which have a strong GK activating effect and high solubility in water.

Specifically, the present invention is:

(1) to provide a compound of Formula (I) shown below, or a pharmaceutically acceptable salt thereof (hereinafter also referred to as "compound according to the present invention" or "compound of Formula (I)"):

(I)

wherein: $R^1$ represents a group selected from the group consisting of:

a lower alkylsulfonyl group;

a lower alkyl groups substituted with a hydroxy or a lower alkoxy group;

a lower alkoxy group substituted with a hydroxy groups; and a group of Formula (II):

(II)

wherein $R^3$ and $R^4$ each independently represent a hydrogen atom or a lower alkyl group optionally substituted with a hydroxy group, or $R^3$ and $R^4$ together with a nitrogen atom to which they are attached, represent a four- to seven-membered nitrogen-containing aliphatic ring;

$R^2$ represents a hydrogen atom;

$R^{20}$ independently represents a group selected from the group consisting of hydrogen atoms, lower alkyl groups optionally substituted with hydroxy groups, lower alkoxy groups, and groups of Formula (III):

(III)

wherein $R^5$ and $R^6$ each independently represent a hydrogen atom, or a lower alkyl group, or $R^5$ and $R^6$ together with a nitrogen atom to which they are attached represent a four- to seven-membered nitrogen-containing aliphatic ring;

m represents an integer of from 1 to 3;

n represents zero or 1; and

Formula (IV):

(IV)

represents a heteroaryl group selected from the group consisting of pyridinyl, pyrazinyl, and pyrazolyl groups (except that $R^1$ is an ethane sulfonyl group; the group represented by the aforementioned formula (IV) is a pyridinyl group; $R^{20}$ is a hydrogen atom; and m is 3).

Furthermore, the present invention is also:

(2) to provide pharmaceutical compositions including the following (α) to (γ) to be used for treating, preventing and/or delaying the onset of type 2 diabetes mellitus:

(α) compounds presented in the aforementioned formula (I);

(β) one or more compounds selected from the group consisting of the following (a) to (i): (a) other glucokinase activators; (b) biguanides; (c) PPAR agonists; (d) insulin; (e) somatostatins; (f) α-glucosidase inhibitors; (g) insulin secretagogues; (h) DPP-IV inhibitors (dipeptidyl peptidase inhibitors); and (i) glucose uptake facilitators; and (γ) pharmacologically acceptable carriers;

(3) to provide glucokinase activators containing the compounds, presented in the aforementioned formula (I), or the pharmaceutically acceptable salts thereof as active principles;

(4) to provide prophylactic or therapeutic agents for diabetes mellitus containing the compounds, presented in the aforementioned formula (I), or the pharmaceutically acceptable salts thereof as active principles; and (5) to provide pharmaceutical compositions containing the compounds, presented in the aforementioned formula (I), or the pharmaceutically acceptable salts thereof as active principles.

Since the compounds presented in the aforementioned formula (I) has glucokinase-activating effects, they are further useful as therapeutic and/or prophylactic agents for diabetes mellitus, as therapeutic and/or prophylactic agents for chronic complications of diabetes mellitus, such as retinopathy, nephropathy, neurosis, ischemic heart disease and arteriosclerosis, and further as therapeutic and/or prophylactic agents for obesity.

The compounds presented in the aforementioned formula (I) are useful preferably as therapeutic or prophylactic agents for diabetes mellitus, further preferably as therapeutic agents for diabetes mellitus.

The meanings of the terms as used herein will be described, and the compounds according to the present invention will be described in more detail.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Alkoxy group" means a hydroxyl group of which the hydrogen atom is substituted with the above-mentioned lower alkyl group, and includes, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

Example of four- to seven-membered nitrogen-containing aliphatic ring includes azetidinyl group, pyrrolidinyl group, piperidinyl group or homopiperidinyl group.

In order to more specifically disclose compounds of Formula (I) according to the present invention:

Formula (I)

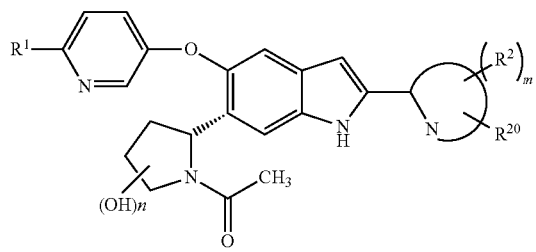

(I)

wherein the symbols have the same meanings as above and the symbols used in Formula (I) are described with reference to specific examples.

$R^1$ represents a group selected from the group consisting of:
a lower alkylsulfonyl group;
a lower alkyl group substituted with hydroxy or lower alkoxy group;
a lower alkoxy group substituted with hydroxy group; and
a group of Formula (II):

(II)

wherein $R^3$ and $R^4$ independently represent a hydrogen atom or a lower alkyl group optionally substituted with a hydroxy group, or $R^3$ and $R^4$ together with a nitrogen atom to which they are attached, represent a four- to seven-membered nitrogen-containing aliphatic ring.

"Lower alkylsulfonyl group" for $R^1$ means a sulfonyl group substituted with the lower alkyl group, specifically, examples of which include a methylsulfonyl, an ethylsulfonyl, a n-propylsulfonyl, a cyclopropylsulfonyl, a n-butylsulfonyl, and a tert-butylsulfonyl group.

"Lower alkyl group substituted with a hydroxy or a lower alkoxy group" for $R^1$ means a lower alkyl group substituted with a hydroxy group or a lower alkyl group substituted with the lower alkoxy group. Examples of "lower alkyl group substituted with a hydroxy group" include a hydroxymethyl, a 1-hydroxyethyl, a 2-hydroxyethyl, and a 3-hydroxypropyl group.

Example of "a lower alkoxy group substituted with a hydroxy group" for $R^1$ includes, specifically, a hydroxy methoxy, a 1-hydroxy ethoxy, a 2-hydroxy ethoxy, and a 3-hydroxy propoxy group.

Example of a group of Formula (II) for $R^1$:

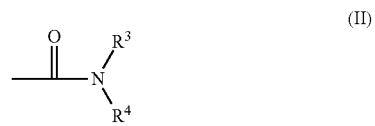

(II)

wherein the symbols have the same meanings as above, include, specifically, a methylcarbamoyl, an ethylcarbamoyl, an isopropylcarbamoyl, a n-propylcarbamoyl, a dimethylcarbamoyl, a diethylcarbamoyl, an ethylmethylcarbamoyl, an 1-azetidinylcarbamoyl, a 1-pyrrolidinylcarbamoyl, a 1-piperidinylcarbamoyl, and a 2-hydroxyethyl-methylcarbamoyl group.

A group of $R^1$ includes a lower alkylsulfonyl group and a lower alkoxy group substituted with a hydroxy or lower alkyl group.

$R^2$ represents a hydrogen atom.

$R^{20}$ represents a group selected from the group consisting of:
a hydrogen atoms;
a lower alkyl group optionally substituted with a hydroxy group,
a lower alkoxy group, and
a groups of Formula (III):

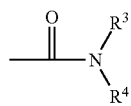

(III)

wherein $R^5$ and $R^6$ independently represent a hydrogen atom, or a lower alkyl group optionally substituted with a hydroxy group), or $R^5$ and $R^6$ together with a nitrogen atom to which they are attached represent a four- to seven-membered nitrogen-containing aliphatic ring.

"Lower alkyl group optionally substituted with a hydroxy group" for $R^{20}$ represents an unsubstituted lower alkyl group or a lower alkyl group substituted with a hydroxy group.

"Unsubstituted lower alkyl group" have the same meanings the as "lower alkyl group" defined above, specifically, examples of which include a methyl, an ethyl, and an isopropyl group.

"Lower alkyl group substituted with a hydroxy group" means the lower alkyl group substituted with a hydroxy group, defined above, specifically, examples of which include a hydroxymethyl, a 1-hydroxyethyl, a 2-hydroxyethyl, a 3-hydroxypropyl, and a 1-hydroxy-1-methylethyl group.

"Lower alkyl group optionally substituted with a hydroxy group for $R^{20}$ is preferably a lower alkyl group substituted with a hydroxy group.

"Lower alkoxy group" for $R^{20}$ have the same meanings as "lower alkoxy group" defined above, specifically, examples of which include a methoxy, an ethoxy, a propoxy, and an isopropoxy group.

Example of a group of Formula (III) for $R^{20}$:

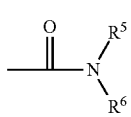

(III)

wherein the symbols have the same meanings as above, include, specifically, a methylcarbamoyl, an ethylcarbamoyl, an isopropylcarbamoyl, a n-propylcarbamoyl, a dimethylcarbamoyl, a diethylcarbamoyl, an ethylmethylcarbamoyl, an 1-azetidinylcarbamoyl, a 1-pyrrolidinylcarbamoyl, a 1-piperidinylcarbamoyl, and a 2-hydroxyethyl-methylcarbamoyl group.

$R^{20}$ is preferably a hydrogen atom or a lower alkyl group substituted with a hydroxy group, more preferably a lower alkyl group substituted with a hydroxy group.

A group of Formula (IV):

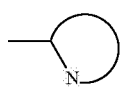

(IV)

means a heteroaryl group selected from the group consisting of a pyridinyl, a pyrazinyl, and a pyrazolyl group, specifically, including a group selected from the group consisting of Formula:

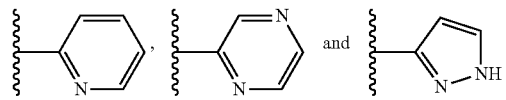

wherein

Formula shows a site attached to an indole ring.

m represents an integer of from 1 to 3, preferably 2 or 3.

n represents zero or 1, preferably zero.

Any of $R^1$, $R^2$, $R^{20}$, $R^3$, $R^4$, $R^5$, $R^6$, m, n, and preferred embodiments of Formula (IV) may be combined.

(A) A preferred embodiment of a compound of the present invention is a compound or a pharmaceutically acceptable salt thereof of the aforementioned formula (I) wherein n is zero.

(B) Also, another preferred embodiment of a compound of the present invention is a compound or a pharmaceutically acceptable salt thereof, of the aforementioned formula (I), wherein $R^{20}$ represents a group selected from the group consisting of a lower alkyl group optionally substituted with a hydroxy group, a lower alkoxy group, and a group of Formula (III):

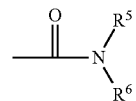

(III)

wherein $R^5$ and $R^6$ independently represent a hydrogen atom, or a lower alkyl group, or $R^5$, $R^6$, and a nitrogen atom, to which they are attached represent a four- to seven-membered nitrogen-containing aliphatic ring; and n is zero.

(C) Also, another preferred embodiment of a compound according to the present invention is a compound or a pharmaceutically acceptable salt thereof, of the aforementioned formula (I), wherein $R^{20}$ represents a lower alkyl group optionally substituted with a hydroxy group, and n is zero.

(D) Also, another preferred embodiment of a compound according to the present invention is a compound or a pharmaceutically acceptable salt thereof, of the aforementioned formula (I), wherein $R^{20}$ represents a group of Formula (III):

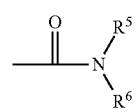

(III)

wherein the symbols have the same meanings as above, and n is zero.

(E) Also, another preferred embodiment of a compound according to the present invention is a compound or a pharmaceutically acceptable salt thereof of the aforementioned formula (I), wherein $R^{20}$ represents a lower alkoxy group and n is zero.

(F) Also, another preferred embodiment of a compound according to the present invention is a compound or a pharmaceutically acceptable salt thereof of the aforementioned formula (I), wherein $R^{20}$ represents a lower alkyl group substituted with a hydroxy group and n is zero.

(G) Also, another preferred embodiment of a compound according to the present invention is a compound according to any one of (B) to (F) described above or a pharmaceutically acceptable salt thereof, wherein $R^1$ represents a lower alkylsulfonyl group.

(G) Also, another preferred embodiment of a compound according to the present invention is a compound according to any one of (B) to (F) described above or a pharmaceutically acceptable salt thereof, wherein a group of the aforementioned formula (IV) is a group of Formula (IV-1):

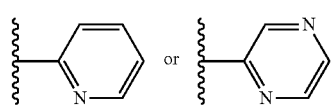

(IV-1)

wherein:

formula has the same meaning as above.

(I) Also, another preferred embodiment of a compound according to the present invention is a compound according to any one of (B) to (F) described above or a pharmaceutically acceptable salt thereof, wherein R¹ represents a lower alkylsulfonyl group and a group of the aforementioned formula (IV) is a group of the aforementioned formula (IV-1).

(J) Also, another preferred embodiment of a compound according to the present invention is a compound or a pharmaceutically acceptable salt thereof of the aforementioned formula (I), wherein $R^{20}$ represents a hydrogen atom and n is zero.

(K) Also, another preferred embodiment of a compound according to the present invention is a compound according to (J) described above or a pharmaceutically acceptable salt thereof of the aforementioned formula (I), wherein R¹ represents a lower alkylsulfonyl group.

(L) Also, another preferred embodiment of a compound according to the present invention is a compound according to (K) described above or a pharmaceutically acceptable salt thereof, wherein a group of the aforementioned formula (IV) is a group of the aforementioned formula (IV-1).

(M) In another preferred embodiment of a compound according to the present invention, a compound of the aforementioned formula (I) is also a compound selected from the group consisting of 6-[(R)-1-acetylpyrrolidin-2-yl]-2-(4-hydroxymethylpyridin-2-yl)-5-(6-methylsulfonylpyridin-3-yloxy)-1H-indole, 6-[(R)-1-acetylpyrrolidin-2-yl]-5-(6-methylsulfonylpyridin-3-yloxy)-2-(5-methylpyrazin-2-yl)-1H-indole, 6-[(R)-1-acetylpyrrolidin-2-yl]-2-(1-methyl-1H-pyrazol-3-yl)-5-(6-methylsulfonylpyridin-3-yloxy)-1H-indole, 6-[(R)-1-acetylpyrrolidin-2-yl]-2-[5-(N-methylcarbamoyl)pyridin-2-yl]-5-(6-methylsulfonylpyridin-3-yloxy)-1H-indole, 6-[(R)-1-acetylpyrrolidin-2-yl]-5-(6-hydroxymethylpyridin-3-yloxy)-2-(5-methylpyrazin-2-yl)-1H-indole, 6-[(R)-1-acetylpyrrolidin-2-yl]-2-[5-(1,1-dimethylhydroxymethyl)pyridin-2-yl]-5-(6-hydroxymethylpyridin-3-yloxy)-1H-indole, 6-[(R)-1-acetylpyrrolidin-2-yl]-2-[5-(1,1-dimethylhydroxymethyl)pyridin-2-yl]-5-(6-methylsulfonylpyridin-3-yloxy)-1H-indole, 6-[(R)-1-acetylpyrrolidin-2-yl]-2-(5-hydroxymethylpyrazin-2-yl)-5-(6-methylsulfonylpyridin-3-yloxy)-1H-indole, 6-[(R)-1-acetylpyrrolidin-2-yl]-5-[6-(2-hydroxyethoxy)pyridin-3-yloxy]-2-(5-methylpyrazin-2-yl)-1H-indole, 6-[(R)-1-acetylpyrrolidin-2-yl]-5-[6-(2-hydroxyethoxy)pyridin-3-yloxy]-2-(5-hydroxymethylpyrazin-2-yl)-1H-indole, 6-[(R)-1-acetylpyrrolidin-2-yl]-2-(5-hydroxymethylpyridin-2-yl)-5-(6-methoxymethylpyridin-3-yloxy)-1H-indole, 6-[(R)-1-acetylpyrrolidin-2-yl]-2-(5-hydroxymethylpyrazin-2-yl)-5-(6-methoxymethylpyridin-3-yloxy)-1H-indole, 6-[(R)-1-acetylpyrrolidin-2-yl]-5-[6-(azetidin-1-ylcarbonyl)pyridin-3-yloxy]-2-[5-(1,1-dimethylhydroxymethyl)pyrazin-2-yl]-1H-indole, 6-[(R)-1-acetylpyrrolidin-2-yl]-2-[5-(1,1-dimethylhydroxymethyl)pyrazin-2-yl]-5-(6-methylsulfonylpyridin-3-yloxy)-1H-indole, 6-[(R)-1-acetylpyrrolidin-2-yl]-5-[6-(azetidin-1-ylcarbonyl)pyridin-3-yloxy]-2-(5-hydroxymethylpyridin-2-yl)-1H-indole, and 6-[(R)-1-acetylpyrrolidin-2-yl]-5-[6-(azetidin-1-ylcarbonyl)pyridin-3-yloxy]-2-[5-(1,1-dimethylhydroxymethyl)pyridin-2-yl]-1H-indole; or a pharmaceutically acceptable salt thereof (N) In another preferred embodiment of a compound according to the present invention, a compound of the aforementioned formula (I) is also a compound selected from the group consisting of 6-[(R)-1-acetylpyrrolidin-2-yl]-5-(6-methylsulfonylpyridin-3-yloxy)-2-(pyrazin-2-yl)-1H-indole, 6-[(R)-1-acetylpyrrolidin-2-yl]-5-(6-hydroxymethylpyridin-3-yloxy)-2-(pyrazin-2-yl)-1H-indole, 6-[(R)-1-acetylpyrrolidin-2-yl]-5-[6-(2-hydroxyethoxy)pyridin-3-yloxy]-2-(pyridin-2-yl)-1H-indole, 6-[(R)-1-acetylpyrrolidin-2-yl]-5-[6-(2-hydroxyethoxy)pyridin-3-yloxy]-2-(pyrazin-2-yl)-1H-indole, 6-[(R)-1-acetylpyrrolidin-2-yl]-5-(6-methoxymethylpyridin-3-yloxy)-2-(pyrazin-2-yl)-1H-indole, 6-[(R)-1-acetylpyrrolidin-2-yl]-5-(6-methoxymethylpyridin-3-yloxy)-2-(pyridin-2-yl)-1H-indole, 6-[(R)-1-acetylpyrrolidin-2-yl]-5-[6-(2-hydroxyethyl)pyridin-3-yloxy]-2-(pyrazin-2-yl)-1H-indole, 6-[(R)-1-acetylpyrrolidin-2-yl]-5-[6-(azetidin-1-ylcarbonyppyridin-3-yloxy)-2-(pyrazin-2-yl)-1H-indole, 6-[(R)-1-acetylpyrrolidin-2-yl]-5-[6-(N,N-dimethylcarbamoyl)pyridin-3-yloxy]-2-(pyrazin-2-yl)-1H-indole, 6-[(R)-1-acetylpyrrolidin-2-yl]-5-[6-(N-ethylcarbamoyl)pyridin-3-yloxy]-2-(pyrazin-2-yl)-1H-indole, 6-[(R)-1-acetylpyrrolidin-2-yl]-5-[6-(N,N-diethylcarbamoyl)pyridin-3-yloxy]-2-(pyrazin-2-yl)-1H-indole, and 6-[(R)-1-acetylpyrrolidin-2-yl]-5-{6-[N-(2-hydroxyethyl)]-N-methylcarbamoyl]pyridin-3-yloxy}-2-(pyrazin-2-yl)-1H-indole; or a pharmaceutically acceptable salt thereof.

A compound of Formula (I) according to the present invention:

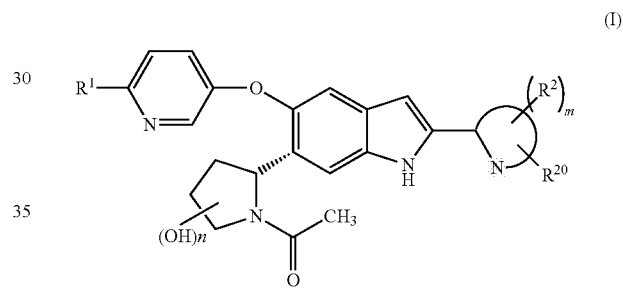

wherein the symbols have the same meanings as above, respectively, may be produced, e.g., by the following process:

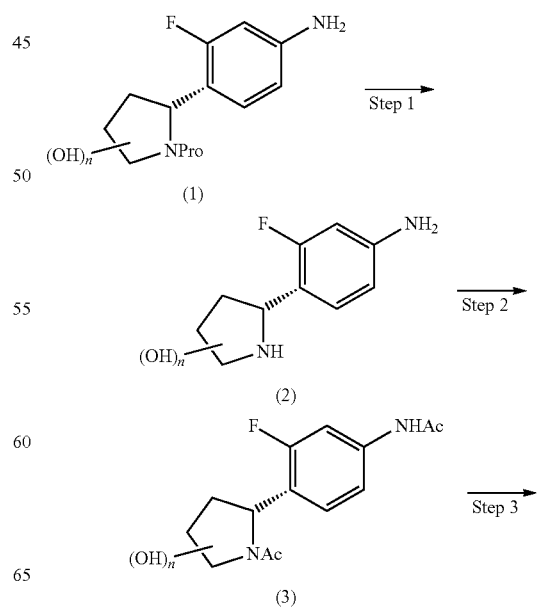

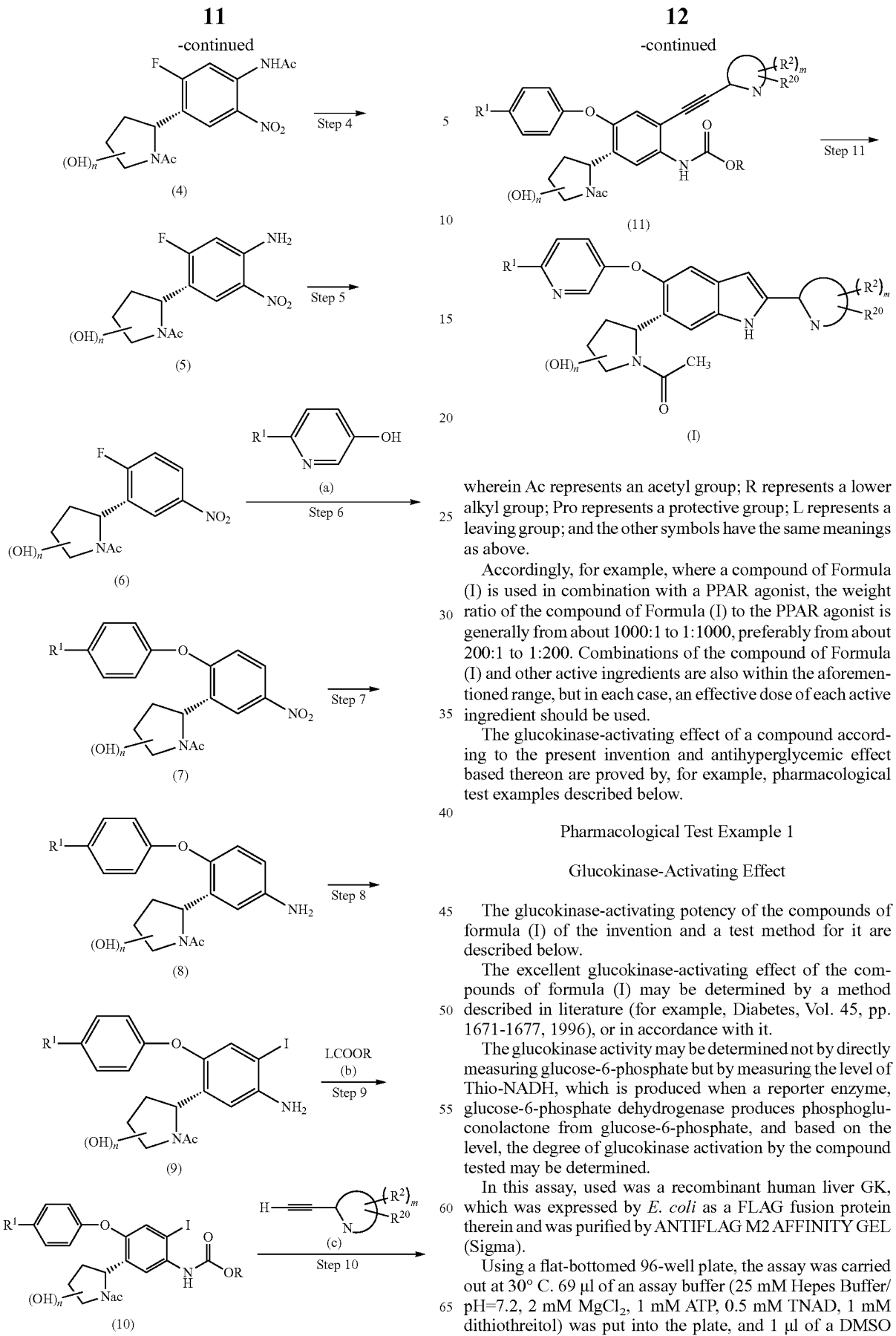

wherein Ac represents an acetyl group; R represents a lower alkyl group; Pro represents a protective group; L represents a leaving group; and the other symbols have the same meanings as above.

Accordingly, for example, where a compound of Formula (I) is used in combination with a PPAR agonist, the weight ratio of the compound of Formula (I) to the PPAR agonist is generally from about 1000:1 to 1:1000, preferably from about 200:1 to 1:200. Combinations of the compound of Formula (I) and other active ingredients are also within the aforementioned range, but in each case, an effective dose of each active ingredient should be used.

The glucokinase-activating effect of a compound according to the present invention and antihyperglycemic effect based thereon are proved by, for example, pharmacological test examples described below.

Pharmacological Test Example 1

Glucokinase-Activating Effect

The glucokinase-activating potency of the compounds of formula (I) of the invention and a test method for it are described below.

The excellent glucokinase-activating effect of the compounds of formula (I) may be determined by a method described in literature (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on the level, the degree of glucokinase activation by the compound tested may be determined.

In this assay, used was a recombinant human liver GK, which was expressed by $E.\ coli$ as a FLAG fusion protein therein and was purified by ANTIFLAG M2 AFFINITY GEL (Sigma).

Using a flat-bottomed 96-well plate, the assay was carried out at 30° C. 69 μl of an assay buffer (25 mM Hepes Buffer/pH=7.2, 2 mM $MgCl_2$, 1 mM ATP, 0.5 mM TNAD, 1 mM dithiothreitol) was put into the plate, and 1 μl of a DMSO solution of the compound or DMSO alone as a control was added thereto. Next, 20 µl of an enzyme mixture (FLAG-GK, 20 U/ml G6PDH) cooled in ice was added to it, and 10 µl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for assessing the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (µM) were computed and used as the index of the GK-activating potency of the compound.

The GK activating potency of the compounds of the invention was measured according to the method as above, and the results are shown in Table 5 below.

TABLE 5

| Compound No. | Emax (%) | EC50 (µM) |
|---|---|---|
| Example 1 | 1110 | 0.19 |
| Example 2 | 1026 | 0.09 |
| Example 3 | 1022 | 0.12 |
| Example 4 | 943 | 0.18 |
| Example 7 | 1005 | 0.12 |
| Example 9 | 1070 | 0.13 |
| Example 10 | 1066 | 0.11 |
| Example 13 | 995 | 0.23 |
| Example 15 | 849 | 0.13 |
| Example 16 | 1105 | 0.17 |
| Example 17 | 988 | 0.08 |
| Example 26 | 942 | 0.16 |
| Example 27 | 957 | 0.12 |
| Example 28 | 1051 | 0.10 |

Accordingly, the compounds of the invention have an excellent GK activating potency indicated by $E_{max}$ and $EC_{50}$, as in the above Table.

The antihyperglycemic effect of the compound according to the present invention, and a test method therefor will now be explained.

Pharmacological Test Example 2

Antihyperglycemic Effect

Six-week-old male C57BL/6J mice were fed a high-fat diet (RESEARCH DIETS, D12492) for ≥9 weeks to produce the high-fat diet loaded mice (>160 mg/dl).

The slight tail tips of the high-fat diet loaded mice (13 weeks old, n=6) under the conditions of free-feeding and water intake were cut with scissors to collect their blood. The collected blood was used to determine blood glucose levels prior to the administration of a compound by a blood glucose level measuring apparatus (One Touch Ultra (Johnson Johnson)), followed by oral administration of the compound suspended in a 0.5% methyl cellulose solution at 10 mg/kg, while a 0.5% methyl cellulose solution was orally administered to the control group. The blood glucose levels were determined using the blood glucose level measuring apparatus every 1 hour after the administration of the test drug solutions.

The values of the decreases in blood glucose (differences between the control group and the compound-treated group) at 1 hour after administration were shown in Table 6 described below.

The values of the decreases in blood glucose (differences between the control group and the compound-treated group) at 1 hour after administration of the compounds according to Example 1 were shown in Table 6 described below.

TABLE 6

| Example No. | Difference in blood glucose level from control group (Δmg/dl) |
|---|---|
| Example 1 | −72 |

Pharmacological Test Example 3

Antihyperglycemic Effect

From the cephalic vein of male beagles fasted overnight (10.0-14.6 kg body weight), blood was collected prior to administration, followed by oral administration of the test drug suspended in a 0.5% methyl cellulose solution (0.3 and 1 mg/kg), while a 0.5% methyl cellulose solution was orally administered to the control group. The blood was collected at 0.5, 1, 2, and 4 hours after the administration of the test drug. Plasma was separated from the obtained blood to determine a plasma glucose level using Determina-GL-E (Kyowa Medics).

Percentage reduction in plasma glucose level AUC compared to the control group up to 4 hours after the administration of the compounds according to Example 1 was described below.

TABLE 7

| Example compound | Dose (mg/kg) | Rate of decrease in plasma glucose level AUC (%) |
|---|---|---|
| Example 1 | 0.3 | 15.9 |
|  | 1 | 27.4 |

These reveal that the compounds according to the present invention have excellent antihyperglycemic effect.

The solubilities of the compounds according to the present invention in water and a testing method thereof will now be explained.

Solubility in Water

For solubility in water, the solubility of a compound in water was determined by a solution precipitation method.

For an HPLC system, Agilent HPLC 1100 system was used. For a column, Agilent Zorbax Eclipse C18 (inside diameter of 4.6 mm, length of 50 mm, and particle diameter of 1.8 µm) was used. For a shaker, Microincubator M-36 (Taitec) was used. For a plate, a 96-deep well plate (Nunc. 260252) was used. For a well cap, Pre-Slit Well Cap for 96 Well PP (NALGENE. 276011) was used. For a filtration plate, Multi-Screen Solubility (Millipore; MSSLBPC10) was used. For dispensation, an 8-channel electronic multipipette, Biohit Proline (Biohit), and a 96-well automatic pipetting device, Biomeck 2000 (Biomeck) were used. For a reagent used, a pure solvent for DMSO ultraviolet absorption spectrum (Dojindo 349-01025) and water (MiliQ water, manufactured by Millipore).

Procedures are described below.

1. Preparation of Dmso Solution

For a DMSO solution, a sample was prepared with DMSO to be precisely 10 mM.

2. Preparation of Sample Solution

Precise dispensation of 10 µL of a DMSO solution into each well of a 96-well plate was performed. Following addition of 490 µL of water to each of the wells and plate-sealing with 96-well Cap (Agilent No. 5042-1389), intense stirring processing of the plate was performed for 60 minutes at room temperature on a shaker. Subsequently, 200 µL of a treatment sample was added to a plate for centrifugal filtration, and centrifugal filtration of the sample was performed to obtain a filtrate. A sample solution was made by adding 200 µl, of a 50% aqueous acetonitrile solution to the provided filtrate.

3. Preparation of Sample for Creating Calibration Curve

Precise dispensation of 10 µL of a DMSO solution into each well of a 96-well plate was performed. An appropriate amount of a 50% aqueous acetonitrile solution was added to each DMSO solution, and this mixture, prepared to have a concentration of 1 µm to 200 µM, was used as a standard solution.

Settings for HPLC measurement are described below.

Detection was performed using a multi-wavelength detector (190-370 nm). For a column, the above-mentioned column was used at 40° C. A flow rate was set at 1.2 ml/min, and an amount of an injected sample at 20 µL. For a moving phase, a 0.1% aqueous phosphoric acid solution as a liquid A and acetonitrile as a liquid B were used to carry out analyses in accordance with a time schedule described below.

TABLE 8

| Time (min) | A % | B % |
| --- | --- | --- |
| 0.0 | 95 | 5 |
| 4.0 | 20 | 80 |
| 4.1 | 95 | 5 |
| 7.0 | stop | |

For the analyses, the data of UV 275 nm were adopted. Obtained chromatography levels were integrated to create a calibration curve from Area of samples (1, 10, 50, and 200 µM) for creating a calibration curve. Using the calibration curve, regression calculation of concentrations in water was carried out from Area of sample solutions (water).

The solubilities of compounds according to the present invention in water were determined by this method.

The results are shown below.

TABLE 9-1

| Example No, | Solubility (µM) |
| --- | --- |
| Example 1 | >170 |
| Example 2 | >170 |
| Example 3 | >170 |
| Example 4 | >170 |
| Example 5 | 111.5 |
| Example 6 | >170 |
| Example 7 | >170 |
| Example 8 | >170 |
| Example 9 | 151.8 |
| Example 10 | 95.1 |

TABLE 9-2

| Example 11 | 48.6 |
| --- | --- |
| Example 12 | 128 |
| Example 13 | 93.7 |
| Example 14 | >170 |
| Example 15 | 168 |
| Example 16 | >170 |
| Example 17 | >170 |
| Example 18 | 132.9 |
| Example 19 | >170 |
| Example 20 | 122.5 |
| Example 21 | >170 |
| Example 22 | >170 |

TABLE 9-2-continued

| Example 23 | 77.6 |
| --- | --- |
| Example 24 | 141.9 |
| Example 25 | >170 |
| Example 26 | 128.9 |
| Example 27 | >170 |
| Example 28 | >170 |

Also, the solubilities of example compounds, disclosed in WO 2007/037534, in water were determined by this method. The results are shown below.

TABLE 10

| Example No. | Solubility (µM) |
| --- | --- |
| Example 1 | <1.0 |
| Example 2 | 4.6 |
| Example 3 | 16.9 |
| Example 5 | 29.9 |
| Example 7 | 10.4 |
| Example 8 | 1.2 |

As is apparent from tables 9-1, 9-2, and 10, described above, the compounds according to the present invention notably improves the compounds disclosed in WO 2007/037534 in solubility in water and are excellent as medicines.

An acetyl pyrrolidinyl indole derivative according to the present invention presented in Formula (I) or a pharmaceutically acceptable salt thereof has a strong glucokinase-activating effect, and are useful for treatment and/or prevention of diabetes mellitus, diabetes mellitus complications, or obesity. A compound according to the present invention also has adequate solid state properties, in particular, solubility in water, and is excellent as a medicine.

A compound according to the present invention is suitable for both types of diabetes mellitus, insulin-dependent diabetes mellitus (IDDM) and non-insulin dependent diabetes mellitus (NIDDM).

As used herein, a diabetes mellitus complication refers to a disease accompanying due to the onset of diabetes mellitus. Specifically, examples of diabetes mellitus complications include diabetic nephropathy, diabetic retinopathy, diabetic neuropathy, and diabetic arteriosclerosis.

The present invention will now be explained in more detail referring to Formulation Examples, Examples, and Reference Examples, with the understanding that the invention is in no way limited to these examples.

EXAMPLES

Formulation Example 1

Ten parts of the compound of Example 1, 15 parts of heavy magnesium oxide, and 75 parts of lactose were uniformly mixed to prepare a pulverulent or subtle granular powder with a size of no greater than 350 µm. The powder was placed in capsule containers to prepare capsules.

Formulation Example 2

Following uniform mixing of 45 parts of the compound according to Example 1, 15 parts of starch, 16 parts of lactose, 21 parts of microcrystalline cellulose, 3 parts of polyvinyl alcohol, and 30 parts of distilled water, the mixture was crushed, granulated, dried, and then filtered to prepare granules having sizes with diameters of 1,410 to 177 µm.

Formulation Example 3

Following production of granules by the same method as in Formulation Example 2, 3 parts of calcium stearate was added with respect to 96 parts of the granules and the mixture was compressively formed to prepare tablets with diameters of 10 mm.

Formulation Example 4

Ten parts of microcrystalline cellulose and 3 parts of calcium stearate were added with respect to 90 parts of the granules obtained by the method in Formulation Example 2, and the mixture was compressively formed to produce tablets with diameters of 8 mm, followed by adding a mixed suspension of syrup gelatin and sedimentary calcium carbonate to the tablets to prepare sugar-coated tablets.

The thin-layer chromatography carried out in the examples employed Silicagel 60F245 (Merck) as a plate, in which amine thin-layer chromatography employed PLC05 NH (FUJI Silysia) as a plate and a UV detector was used as a detection method. The column silica gel used was Wakogel TMC-300 (Wako Pure Chemical Industries), and the reverse-phase column silica gel used was LC-SORBTMSP-B-ODS (Chemco) or YMC-GELTMODS-AQ120-S50 (Yamamura Kagaku Kenkyujo).

The abbreviations in the examples described below are described below.
i-Bu: isobutyl
n-Bu: n-butyl
t-Bu: t-butyl
Me: methyl
Et: ethyl
Ph: phenyl
i-Pr: isopropyl
n-Pr: n-propyl
CDC13: heavy chloroform
CD3OD: heavy methanol
DMSO-d6: heavy dimethylsulfoxide Example 1

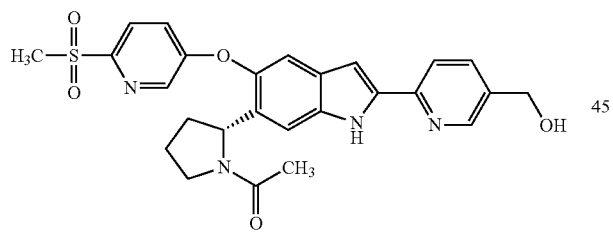

Synthesis of 6[(R)-1-acetylpyrrolidin-2-yl]-2-(4-hydroxymethylpyridin-2-yl)-5-(6-methylsulfonylpyridin-3-yloxy)-1H-indole (Step 1)

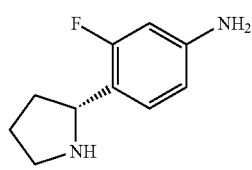

A 4N dioxan hydrochloride solution (200 ml) was added to a methanol solution (100 ml) of (R)-2-(4-amino-2-fluorophenyl)pyrrolidin-1-carboxylic acid tert-butyl ester (30 g, 107 mmol) adjusted by a method described in the literature (Artis, K.; KeVin, R. C.; Jacob, H. W.; Daniel, Z.; Peter, G. D.; Cheng-yl, C. J. Org. Chem. 2008, 73, 4986), and this mixture was stirred for 1 hour at room temperature. The reaction liquid was concentrated under reduced pressure to obtain a white solid containing (R)-2-(4-amino-2-fluorophenyl)pyrrolidine, which was used in the subsequent step without being purified.

(Step 2)

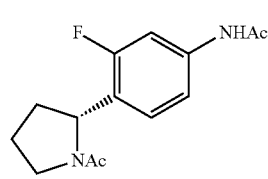

Acetic anhydride (25.4 ml, 269 mmol) was added to a white solid pyridine (100 ml) solution, obtained in step 1, with stirring under ice cooling, and this mixture was stirred for 1 hour at room temperature. Chloroform and a saturated aqueous sodium bicarbonate solution were added to a residue provided by concentrating the reaction liquid under reduced pressure. The organic layer was washed with a saturated saline solution and dried with anhydrous magnesium sulfate, followed by being concentrated under reduced pressure to obtain a white solid containing (R)-1-acetyl-2-(4-acetylamino-2-fluorophenyl)pyrrolidine, which was used in the subsequent step without being purified.

(Step 3)

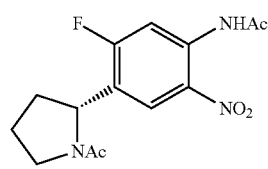

A white solid obtained in step 2 was added to fuming nitric acid (25 ml) for 30 minutes with stirring under ice cooling, and this mixture was stirred for 30 minutes at room temperature. The reaction liquid was neutralized with a saturated aqueous sodium carbonate solution, followed by adding chloroform to the liquid. The organic layer was washed with a saturated saline solution and dried with anhydrous magnesium sulfate, followed by being concentrated under reduced pressure to obtain a yellow oily matter containing (R)-1-acetyl-2-(4-acetylamino-2-fluoro-5-nitrophenyl)pyrrolidine, which was used in the subsequent step without being further purified.

The analytical data of the title compound are shown below.

1H-NMR (CD3OD) δ: 1.90 (2H, s), 1.98 (3H, m), 2.03 (2H, s), 2.18 (2H, s), 2.43 (1H, m), 3.72 (1.3H, m), 3.91 (0.7H, m), 5.22 (1.3H, m), 5.38 (0.7H, m), 7.90 (1H, m), 8.15 (1.3H, d, J=12.7 Hz), 8.26 (0.7H, d, J=12.7 Hz).

ESI-MS (m/e): 310 [M+H]+

(Step 4)

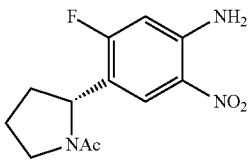

A 5N aqueous sodium hydroxide solution (32.1 ml, 160 mmol) was added to the mixed solution of the yellow oily matter, obtained in step 3, with tetrahydrofuran (60 ml), methanol (60 ml), and water (60 ml) with stirring under ice cooling, and this mixture was stirred for 1 hour at room temperature. A 5N aqueous hydrochloric acid solution (321 ml, 160 mmol) was added to the reaction liquid, this mixture was concentrated under reduced pressure, and chloroform and a saturated aqueous sodium bicarbonate solution were added to a provided residue. The organic layer was washed with a saturated saline solution and dried with anhydrous magnesium sulfate, followed by being concentrated under reduced pressure to obtain a residue and purifying the residue by silica gel column chromatography (MORITEX, Purif-pack SI, chloroform:ethyl acetate=1:1) to obtain (R)-1-acetyl-2-(4-amino-2-fluoro-5-nitrophenyl)pyrrolidine (23.45 g, yield: 81.9%) as a pale yellow solid.

The analytical data of the title compound are shown below.

1H-NMR (CD3OD) δ: 1.88 (1H, s), 1.91 (3H, m), 2.11 (2H, s), 2.29 (1H, m), 3.62 (1.5H, m), 3.79 (0.5H, m), 5.12 (1H, m), 6.67 (1H, m), 7.73 (1H, m).

ESI-MS (m/e): 268 [M+H]+

(Step 5)

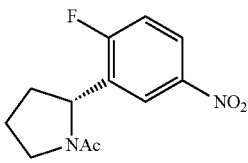

An aqueous solution (60 ml) of sodium nitrite (7.25 g, 105 mmol) was dropped to a mixed solution of the compound (23.4 g, 88 mmol), obtained in step 4, with dioxan (300 ml), water (220 ml), and a 4N dioxan hydrochloride solution (22 ml) for 20 minutes with stirring under ice cooling, and this mixture was stirred for 30 minutes under ice cooling. A 50% aqueous hypophosphorous acid solution (60 ml) was dropped to the reaction liquid for 15 minutes with stirring under ice cooling, and this mixture was stirred for 30 minutes under ice cooling, followed by being stirred for 1 hour at room temperature. Chloroform and a saturated aqueous sodium bicarbonate solution were added to the reaction liquid, and the organic layer was washed with a saturated saline solution and dried with anhydrous magnesium sulfate, followed by being concentrated under reduced pressure. The obtained residue was purified by silica gel column chromatography (MORITEX, Purif-pack SI, hexan:ethyl acetate=1:3) to obtain (R)-1-acetyl-2-(2-fluoro-5-nitrophenyl)pyrrolidine (18.81 g, yield: 85.1%) as a yellow oily matter.

The analytical data of the title compound are shown below.

1H-NMR (CD3OD) δ: 1.93 (1H, s), 1.96 (3H, m), 2.15 (2H, s), 2.33 (1H, m), 3.73 (2H, m), 5.26 (1H, m), 7.22 (1H, m), 7.94 (1H, m), 8.13 (1H, m).

ESI-MS (m/e): 253 [M+H]+

(Step 6)

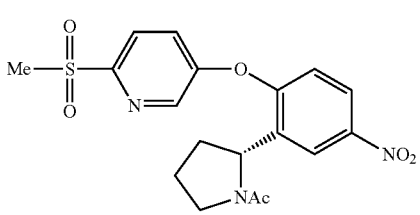

6-(methylsulfonyl)-3-pyridinol (12.7 g, 73.3 mmol) and potassium carbonate (17.15 g, 124 mmol) are added to a N,N-dimethylformamide (150 ml) solution of a compound (14.23 g, 56.4 mmol) obtained in step 5, and this mixture was stirred for 2 hours at 120° C. Ethyl acetate and water were added to the reaction liquid, and the organic layer was washed with a saturated saline solution and dried with anhydrous magnesium sulfate, followed by being concentrated under reduced pressure to obtain a yellow oily matter containing (R)-1-acetyl-2-[2-(6-methylsulfonylpyridin-3-yloxy)-5-nitrophenyl]pyrrolidine and using the matter in the subsequent step without being further purified.

(Step 7)

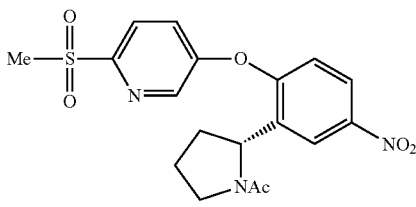

A 10% palladium carbon catalyst (3 g) was added to the mixed solution of the yellow oily matter (14.23 g, 56.4 mmol), obtained in step 6, with tetrahydrofuran (120 ml) and methanol (120 ml), and this mixture was stirred for 14 hours at room temperature under hydrogen atmosphere. Following filtration of the catalyst, a filtrate was concentrated under reduced pressure to obtain a yellow oily matter containing (R)-1-acetyl-2-[5-amino-2-(6-methylsulfonylpyridin-3-yloxy)phenyl]pyrrolidine, which is used matter in the subsequent step without being further purified.

The analytical data of the title compound are shown below.

1H-NMR (CD3OD) δ: 1.83 (1.5H, s), 1.96 (3H, m), 2.03 (1.5H, s), 2.36 (1H, m), 3.22 (3H, s), 3.73 (2H, m), 5.08 (1H, m), 6.58 (1H, m), 6.73 (1H, m), 6.88 (1H, m), 7.49 (1H, m), 8.06 (1H, m), 8.46 (1H, m).

ESI-MS (m/e): 376 [M+H]+

(Step 8)

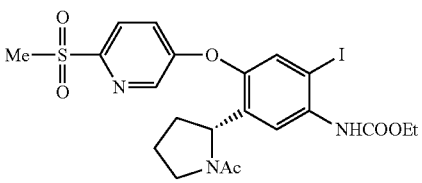

Potassium iodide (8.73 g, 52.6 mmol), potassium iodate (5.63 g, 26.3 mmol), and a 5N aqueous hydrochloric acid solution (16 ml) were sequentially added to the mixed solution of a yellow oily matter, obtained in step 7, with methanol (300 ml), dioxan (240 ml), and water (240 ml) at 50° C., and this mixture was stirred for 4 hours at 50° C. Chloroform was added to the reaction liquid, sequentially washed with a 20% aqueous sodium thiosulfate solution and a saturated saline solution, and dried with anhydrous magnesium sulfate, followed by being concentrated under reduced pressure to obtain a yellow oily matter.

Ethyl chlorocarbonate (10.06 ml, 105 mmol) was added to a pyridine (100 ml) solution of the yellow oily matter with stirring under ice cooling, and this mixture was stirred overnight at room temperature. The residue was concentrated under reduced pressure, and chloroform and a saturated aqueous sodium bicarbonate solution were added to it. The organic layer was washed with a saturated saline solution and dried with anhydrous magnesium sulfate, followed by being concentrated under reduced pressure to obtain a residue and purifying the residue by silica gel column chromatography (MORITEX, Purif-pack SI, chloroform:acetone=3:1) to obtain (R)-1-acetyl-2-[5-ethoxycarbonylamino-4-iodine-2-(6-methylsulfonylpyridin-3-yloxy)phenyl]pyrrolidine (20.1 g, yield: 66.5%) as a yellow oily matter.

The analytical data of the title compound are shown below.

1H-NMR (CD3OD) δ: 1.34 (3H, t, J=7.2 Hz), 1.87 (1H, s), 1.99 (3H, m), 2.04 (2H, s), 2.38 (1H, m), 3.23 (3H, s), 3.73 (2H, m), 4.22 (2H, q, J=7.2 Hz), 5.17 (1H, m), 7.43 (1H, m), 7.54 (1H, m), 7.62 (1H, m), 8.04 (1H, m), 8.58 (1H, m).

ESI-MS (m/e): 574 [M+H]+ (Step 9)

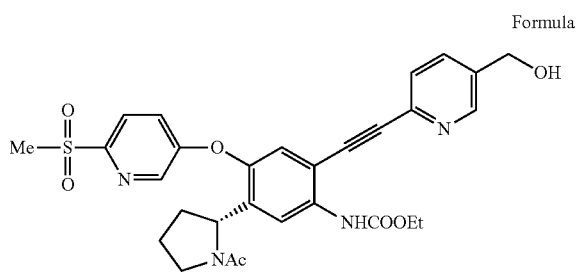

Formula

A bis(triphenylphosphine)palladium(II)dichloride complex (12.2 mg, 0.017 mol) and cuprous iodide (6.6 mg, 0.035 mmol) were added to the mixed solution of the compound (100 mg, 0.174 mmol), obtained in step 8, with tetrahydrofuran (1.5 ml) and triethylamine (2 ml), and a tetrahydrofuran (2 ml) solution of (6-ethynylpyridin-3-yl)methanol (27.9 mg, 0.209 mmol) was dropped with stirring for 5 minutes at 40° C. in nitrogen gas stream. Water and chloroform were added to the reaction liquid under ice cooling to filter insoluble matters. The filtrate was washed with a saturated saline solution and dried with anhydrous magnesium sulfate, followed by being concentrated under reduced pressure. The obtained residue was purified by silica gel column chromatography (MORITEX, Purif-pack NH, hexamacetone=1:1) to obtain (R)-1-acetyl-2-[5-ethoxycarbonylamino-4-(5-hydroxymethylpyridin-2-ylethynyl)-2-(6-methylsulfonylpyridin-3-yloxy) phenyl]pyrrolidine (81 mg, yield: 80.1%) as a pale yellow noncrystal solid.

The analytical data of the title compound are shown below.

1H-NMR (CD3OD) δ: 1.28 (3H, t, J=7.2 Hz), 1.89 (1H, s), 2.06 (3H, m), 2.07 (2H, s), 2.39 (1H, m), 3.23 (3H, s), 3.77 (2H, m), 4.23 (2H, q, J=7.2 Hz), 4.70 (2H, s), 5.22 (1H, m), 7.30 (0.7H, s), 7.38 (0.3H, s), 7.63 (2H, m), 7.88 (1H, m), 7.96 (1H, m), 8.06 (1H, m), 8.59 (1H, m).

ESI-MS (m/e): 579 [M+H]+

(Step 10)

Tetrabutylammonium fluoride (1N tetrahydrofuran solution, 500 μl, 0.5 mmol) were added to a tetrahydrofuran (2 ml) solution of the compound (81 mg, 0.14 mmol) obtained in step 9, and this mixture was stirred for 18 hours at 50° C. Water and chloroform were added to the reaction liquid under ice cooling. The organic layer was washed with a saturated saline solution and dried with anhydrous magnesium sulfate, followed by being concentrated under reduced pressure. The obtained residue was purified by amine-based silica gel column chromatography (MORITEX, Purif-pack NH, hexan:acetone=2:3) to obtain the title compound (34 mg, yield: 47.9%) as a pale yellow noncrystal solid.

The analytical data of the title compound are shown below.

1H-NMR (CD3OD) δ: 1.26 (1H, s), 1.86 (1H, s), 2.03 (3H, m), 2.09 (1H, s), 2.37 (1H, m), 3.22 (3H, s), 3.68 (1H, m), 3.74 (1H, m), 4.70 (2H, s), 5.23 (1H, m), 7.06 (0.5H, s), 7.11 (0.5H, s), 7.38 (2H, m), 7.56 (1H, m), 7.84 (1H, m), 7.92 (1H, m), 8.07 (1H, m), 8.58 (1H, m), 8.61 (1H, m).

ESI-MS (m/e): 507 [M+H]+

Example 2

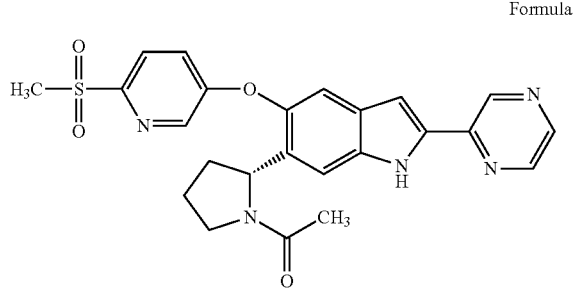 [SMILES: CC(=O)N1CCC[C@@H]1c1cc2[nH]c(-c3cnccn3)cc2cc1Oc1ccc(S(C)(=O)=O)nc1]

Formula

Synthesis of 6-[(R)-1-acetylpyrrolidin-2-yl]-5-(6-methylsulfonylpyridin-3-yloxy)-2-(5-methylpyrazin-2-yl)-1H-indole The title compound (48 mg) was obtained as a pale yellow noncrystal solid by the same method as in Example 1, a method similar thereto, or combinations of them and usual methods, using 2-ethynylpyrazine instead of (6-ethynylpyridin-3-yl) methanol.

The analytical data of the title compound are shown below.

1H-NMRNMR (CD3OD) δ: 1.27 (1H, s), 1.83 (1H, s), 2.03 (3H, m), 2.09 (1H, s), 2.38 (1H, m), 3.22 (3H, s), 3.70 (1H, m), 3.82 (1H, m), 5.23 (1H, m), 7.24 (0.5H, s), 7.28 (0.5H, s), 7.40 (2H, m), 7.58 (1H, m), 8.07 (1H, m), 8.40 (1H, m), 8.58 (1H, m), 8.66 (1H, m), 9.18 (1H, m)

ESI-MS (m/e): 478 [M+H]+

Example 3

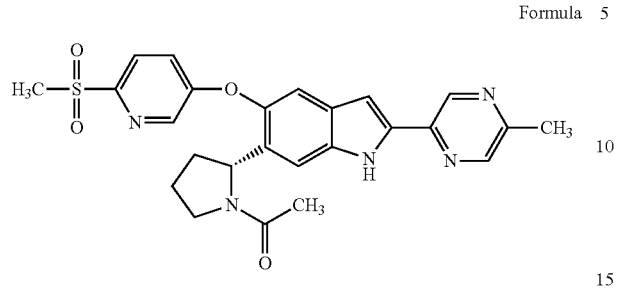

Formula 5

Synthesis of 6-[(R)-1-acetylpyrrolidin-2-yl]-5-(6-methylsulfonylpyridin-3-yloxy)-2-(5-methylpyrazin-2-yl)-1H-indole The title compound (50 mg) was obtained as a pale yellow noncrystal solid by the same method as in Example 1, a method similar thereto, or combinations of them and usual methods, using 2-ethynyl-5-methylpyrazine instead of (6-ethynylpyridin-3-yl)methanol.

The analytical data of the title compound are shown below.
1H-NMR (CD3OD) δ: 1.26 (1H, s), 1.86 (1H, s), 2.04 (3H, m), 2.09 (1H, s), 2.38 (1H, m), 2.59 (2.5H, s), 2.64 (0.5H, s), 3.22 (1.5H, s), 3.23 (1.5H, s), 3.70 (1H, m), 3.82 (1H, m), 5.22 (1H, m), 7.16 (0.5H, s), 7.20 (0.5H, s), 7.39 (2H, m), 7.58 (1H, m), 8.08 (1H, m), 8.59 (2H, m), 9.01 (1H, m).
ESI-MS (m/e): 492 [M+H]+

Example 4

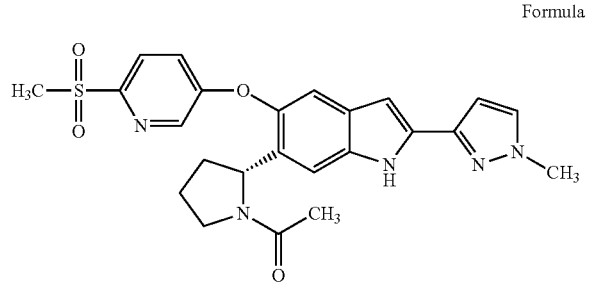

Formula

Synthesis of 6-[(R)-1-acetylpyrrolidin-2-yl]-2-(1-methyl-1H-pyrazol-3-yl)-5-(6-methylsulfonylpyridin-3-yloxy)-1H-indole The title compound (32 mg) was obtained as a pale yellow noncrystal solid by the same method as in Example 1, a method similar thereto, or combinations of them and usual methods, using 3-ethynyl-1-methyl-1H-pyrazole instead of (6-ethynylpyridin-3-yl)methanol.

The analytical data of the title compound are shown below.
1H-NMR (CD3OD) δ: 1.85 (1.5H, s), 1.99 (3H, m), 2.07 (1.5H, s), 2.34 (1H, m), 3.21 (1.5H, s), 3.23 (1.5H, s), 3.64 (1H, m), 3.80 (1H, m), 3.96 (1.5H, s), 3.97 (1.5H, s), 5.22 (1H, m), 6.63 (1H, m), 6.64 (0.5H, s), 6.77 (0.5H, s), 7.23 (1.5H, m), 7.33 (0.5H, m), 7.53 (1H, m), 7.65 (1H, m), 8.06 (1H, m), 8.56 (1H, m).
ESI-MS (m/e): 480 [M+H]+

Example 5

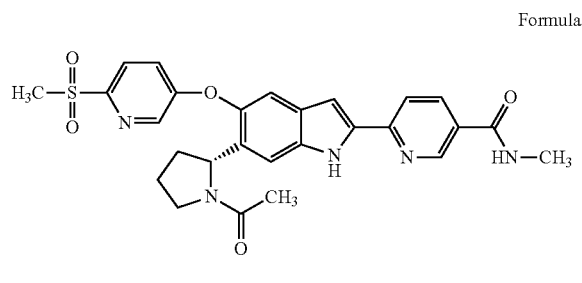

Formula

Synthesis of 6-[(R)-1-acetylpyrrolidin-2-yl]-2-[5-(N-methylcarbamoyl)pyridin-2-yl]-5-(6-methylsulfonylpyridin-3-yloxy)-1H-indole The title compound (45 mg) was obtained as a pale yellow noncrystal solid by the same method as in Example 1, a method similar thereto, or combinations of them and usual methods, using 6-ethynyl-N-methylnicotinamide instead of (6-ethynylpyridin-3-yl)methanol.

The analytical data of the title compound are shown below.
1H-NMR (CD3OD) δ: 1.26 (1H, s), 1.85 (1H, s), 2.03 (3H, m), 2.06 (1H, s), 2.38 (1H, m), 2.98 (3H, s), 3.22 (1.5H, s), 3.23 (1.5H, s), 3.68 (1H, m), 3.88 (1H, m), 5.23 (1H, m), 7.18 (0.5H, s), 7.23 (0.5H, s), 7.36 (1.5H, m), 7.42 (0.5H, s), 7.58 (1H, m), 8.00 (1H, m), 8.06 (1H, m), 8.22 (1H, m), 8.58 (1H, m), 9.03 (1H, m).
ESI-MS (m/e): 534 [M+H]+

Example 6

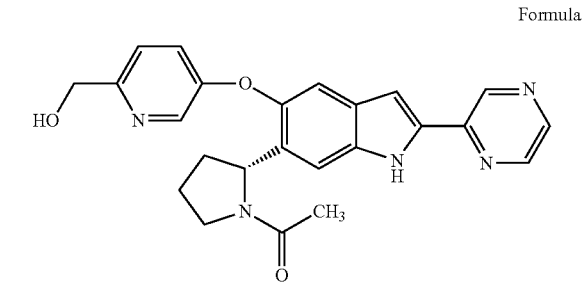 [SMILES: CC(=O)N1CCC[C@@H]1c1cc2[nH]c(-c3cnccn3)cc2cc1Oc1ccc(CO)nc1]

Formula

Synthesis of 6-[(R)-1-acetylpyrrolidin-2-yl]-5-(6-hydroxymethylpyridin-3-yloxy)-2-(pyrazin-2-yl)-1H-indole The title compound (20 mg) was obtained as a pale yellow noncrystal solid by the same method as in Example 1, a method similar thereto, or combinations of them and usual methods, using 5-hydroxy-2-pyridinemethanol instead of 6-(methylsulfonyl)-3-pyridinol and 2-ethynylpyrazine instead of (6-ethynylpyridin-3-yl)methanol.

The analytical data of the title compound are shown below.
1H-NMR (CD3OD) δ: 1.83 (1H, s), 2.03 (3H, m), 2.14 (1H, s), 2.20 (1H, s), 2.38 (1H, m), 3.69 (1H, m), 3.85 (1H, m), 4.69 (2H, s), 5.37 (1H, m), 7.23 (3H, m), 7.51 (2H, m), 8.33 (1H, m), 8.43 (1H, m), 8.62 (1H, m), 9.17 (1H, m).
ESI-MS (m/e): 430 [M+H]+

Example 7

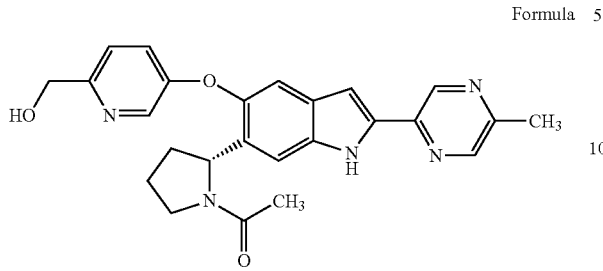

Formula 5

Synthesis of 6-[(R)-1-acetylpyrrolidin-2-yl]-5-(6-hydroxymethylpyridin-3-yloxy)-2-(5-methylpyrazin-2-yl)-1H-indole The title compound (52 mg) was obtained as a pale yellow noncrystal solid by the same method as in Example 1, a method similar thereto, or combinations of them and usual methods, using 5-hydroxy-2-pyridinemethanol instead of 6-(methylsulfonyl)-3-pyridinol and 2-ethynyl-5-methylpyrazine instead of (6-ethynylpyridin-3-yl)methanol.

The analytical data of the title compound are shown below.
1H-NMR (CDCl3) δ: 1.89 (1H, s), 1.98 (3H, m), 2.10 (1H, s), 2.18 (1H, s), 2.38 (1H, m), 2.60 (3H, s), 3.73 (2H, m), 4.72 (0.5H, s), 4.76 (1.5H, s), 5.21 (0.7H, m), 5.39 (0.3H, m), 6.98 (1H, m), 7.24 (3H, m), 8.42 (2H, m), 8.94 (1H, m), 9.38 (0.3H, br-s), 9.51 (0.7H, br-s).
ESI-MS (m/e): 444 [M+H]+

Example 8

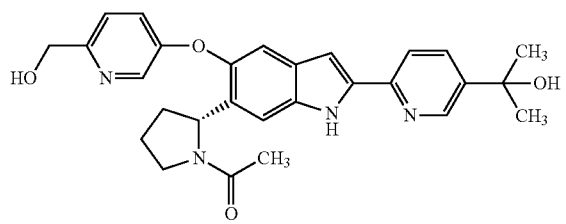

Formula

Synthesis of 6-[(R)-1-acetylpyrrolidin-2-yl]-2-[5-(1,1-dimethylhydroxymethyl)pyridin-2-yl]-5-(6-hydroxymethylpyridin-3-yloxy)-1H-indole The title compound (35 mg) was obtained as a pale yellow noncrystal solid by the same method as in Example 1, a method similar thereto, or combinations of them and usual methods, using 5-hydroxy-2-pyridinemethanol instead of 6-(methylsulfonyl)-3-pyridinol and 2-(6-ethynylpyridin-3-yl)propan-2-ol instead of (6-ethynylpyridin-3-yl)methanol.

The analytical data of the title compound are shown below.
1H-NMR (CDCl3) δ: 1.23 (1H, s), 1.63 (6H, s), 1.82 (1H, s), 1.83 (3H, m), 1.91 (1H, s), 2.21 (1H, m), 3.50 (2H, m), 4.76 (2H, s), 5.22 (1H, m), 6.91 (1H, m), 7.16 (1H, m), 7.35 (3H, m), 7.81 (1H, m), 8.04 (1H, m), 8.41 (1H, m), 8.90 (1H, m), 11.27 (1H, m).
ESI-MS (m/e): 487 [M+H]+

Example 9

Formula

Synthesis of 6-[(R)-1-acetylpyrrolidin-2-yl]-2-[5-(1,1-dimethylhydroxymethyl)pyridin-2-yl]-5-(6-methylsulfonylpyridin-3-yloxy)-1H-indole The title compound (37 mg) was obtained as a pale yellow noncrystal solid by the same method as in Example 1, a method similar thereto, or combinations of them and usual methods, using 2-(6-ethynylpyridin-3-yl)propan-2-ol instead of (6-ethynylpyridin-3-yl)methanol.

The analytical data of the title compound are shown below.
1H-NMR (CD3OD) δ: 1.23 (1H, s), 1.62 (6H, s), 1.84 (1H, s), 2.03 (3H, m), 2.09 (1H, s), 2.38 (1H, m), 3.22 (1.5H, s), 3.23 (1.5H, s), 3.70 (1H, m), 3.83 (1H, m), 5.23 (1H, m), 7.05 (0.5H, s), 7.09 (0.5H, s), 7.33 (1.5H, m), 7.40 (0.5H, s), 7.58 (1H, m), 7.86 (1H, m), 7.98 (1H, m), 8.05 (1H, m), 8.57 (1H, m), 8.79 (1H, m).
ESI-MS (m/e): 535 [M+H]+

Example 10

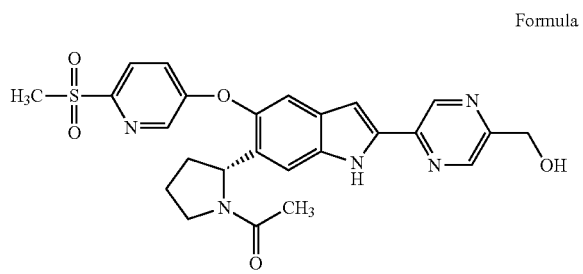

Formula

Synthesis of 6-[(R)-1-acetylpyrrolidin-2-yl]-2-(5-hydroxymethylpyrazin-2-yl)-5-(6-methylsulfonylpyridin-3-yloxy)-1H-indole The title compound (44 mg) was obtained as a pale yellow noncrystal solid by the same method as in Example 1, a method similar thereto, or combinations of them and usual methods, using 2-ethynyl-5-hydroxymethylpyrazine instead of (6-ethynylpyridin-3-yl)methanol.

The analytical data of the title compound are shown below.
1H-NMR (CD3OD) δ: 1.23 (1H, s), 1.83 (1H, s), 1.99 (3H, m), 2.09 (1H, s), 2.38 (1H, m), 3.22 (1.5H, s), 3.23 (1.5H, s), 3.69 (1H, m), 3.84 (1H, m), 4.80 (2H, s), 5.22 (1H, m), 7.21 (0.5H, s), 7.25 (0.5H, s), 7.37 (1.5H, m), 7.43 (0.5H, s), 7.68 (1H, m), 8.06 (1H, m), 8.56 (1H, m), 8.79 (1H, m), 9.07 (1H, m).
ESI-MS (m/e): 508 [M+H]+

Example 11

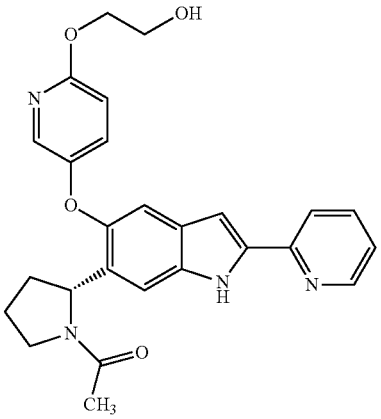

Synthesis of 6-[(R)-1-acetylpyrrolidin-2-yl]-5-[6-(2-hydroxyethoxy)pyridin-3-yloxy]-2-(pyridin-2-yl)-1H-indole The title compound (111 mg) was obtained as a pale yellow solid by the same method as in Example 1, a method similar thereto, or combinations of them and usual methods, using 6-(2-hydroxyethoxy)-pyridin-3-ol instead of 6-(methylsulfonyl)-3-pyridinol and 2-ethynyl-pyridine instead of (6-ethynylpyridin-3-yl)methanol.

The analytical data of the title compound are shown below.

1H-NMR (CDCl3) δ: 1.86 (1.5H, s), 1.83-2.03 (3H, m), 2.14 (1.5H, s), 2.21-2.38 (1H, m), 3.36-3.84 (3H, m), 3.90-3.96 (2H, m), 4.37-4.46 (2H, m), 5.18-5.46 (1H, m), 6.70-6.79 (1H, m), 6.80-6.85 (1H, m), 6.99-7.18 (3H, m), 7.28-7.37 (1H, m), 7.63-7.73 (2H, m), 7.86-7.95 (1H, m), 8.49-8.57 (1H, m), 9.51-9.68 (1H, m).

ESI-MS (m/e): 459 [M+H]+

Example 12

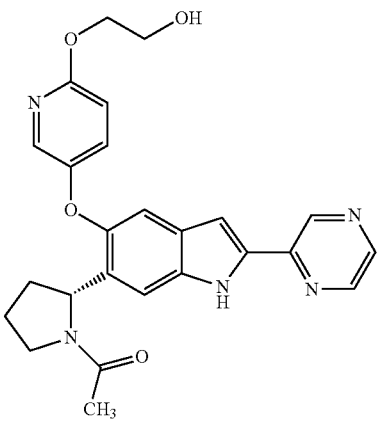

Synthesis of 6-[(R)-1-acetylpyrrolidin-2-yl]-5-[6-(2-hydroxyethoxy)pyridin-3-yloxy]-2-(pyrazin-2-yl)-1H-indole The title compound (23.2 mg) was obtained as a pale brown solid by the same method as in Example 1, a method similar thereto, or combinations of them and usual methods, using 6-(2-hydroxyethoxy)pyridin-3-ol instead of 6-(methylsulfonyl)-3-pyridinol and 2-ethynyl-pyrazine instead of (6-ethynylpyridin-3-yl)methanol.

The analytical data of the title compound are shown below.

1H-NMR (CDCl3) δ: 1.81-2.05 (3H, m), 1.87 (3H, s), 2.10 (1H, s), 2.20-2.43 (1H, m), 3.36 (1H, br-s), 3.53-3.86 (2H, m), 3.89-3.95 (2H, m), 4.38-4.44 (2H, m), 5.23-5.47 (1H, m), 6.73-6.78 (1H, m), 7.00-7.09 (1H, m), 7.16 (1H, s), 7.28-7.36 (1H, m), 7.85-7.94 (1H, m), 8.34-8.40 (1H, m), 8.43-8.49 (1H, m), 8.95-9.01 (1H, m), 9.65-9.26 (1H, m).

ESI-MS (m/e): 460 [M+H]+

Example 13

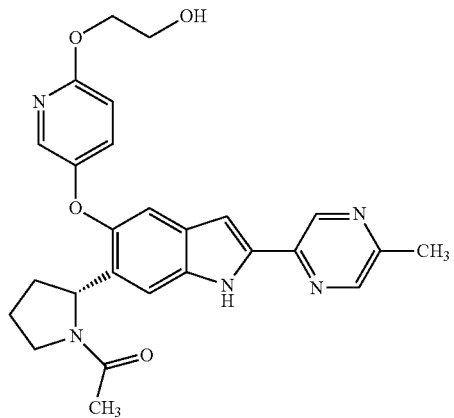

Synthesis of 6-[(R)-1-acetylpyrrolidin-2-yl]-5-[6-(2-hydroxyethoxy)pyridin-3-yloxy]-2-(5-methylpyrazin-2-yl)-1H-indole The title compound (34.2 mg) was obtained as a pale brown solid by the same method as in Example 1, a method similar thereto, or combinations of them and usual methods, using 6-(2-hydroxyethoxy)pyridin-3-ol instead of 6-(methylsulfonyl)-3-pyridinol and 2-ethynyl-5-methylpyrazine instead of (6-ethynylpyridin-3-yl)methanol.

The analytical data of the title compound are shown below.

1H-NMR (CDCl3) δ: 1.82-2.05 (3H, m), 1.87 (1.5H, s), 2.14 (1.5H, s), 2.21-2.41 (1H, m), 2.50-2.62 (3H, m), 3.41-3.43 (1H, m), 3.54-3.86 (2H, m), 3.89-3.97 (2H, m), 4.38-4.46 (2H, m), 5.23-5.47 (1H, m), 6.71-6.81 (1H, m), 6.87-6.93 (1H, m), 6.99-7.16 (2H, m), 7.28-7.37 (1H, m), 7.86-7.95 (1H, m), 8.31-8.40 (1H, m), 8.84-8.92 (1H, m), 9.29-9.57 (1H, m).

ESI-MS (m/e): 474 [M+H]+

Example 14

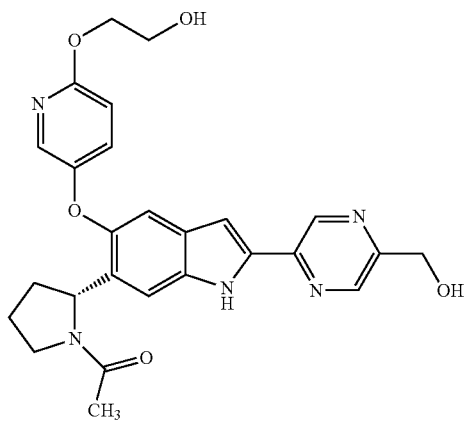

Synthesis of 6-[(R)-1-acetylpyrrolidin-2-yl]-5-[6-(2-hydroxyethoxy)pyridin-3-yloxy]-2-(5-hydroxymethylpyrazin-2-yl)-1H-indole The title compound (31.2 mg) was obtained as a pale brown solid by the same method as in Example 1, a method similar thereto, or combinations of them and usual methods, using 6-(2-hydroxyethoxy)pyridin-3-ol instead of 6-(methylsulfonyl)-3-pyridinol and 2-ethynyl-5-hydroxymethylpyrazine instead of (6-ethynylpyridin-3-yl)methanol.

The analytical data of the title compound are shown below.
1H-NMR (CDCl3) δ: 1.57 (1.5H, s), 1.78-2.07 (3H, m), 1.95 (1.5H, s), 2.18-2.40 (1H, m), 3.28-3.78 (4H, m), 3.87-3.97 (2H, m), 4.39-4.44 (2H, m), 4.77-4.89 (2H, m), 5.21-5.42 (1H, m), 6.69-6.82 (1H, m), 6.92-7.10 (3H, m), 7.28-7.35 (1H, m), 7.84-7.94 (1H, m), 8.50-8.60 (1H, m), 8.91-9.00 (1H, m), 9.73-9.93 (1H, m).
ESI-MS (m/e): 490 [M+H]+

Example 15

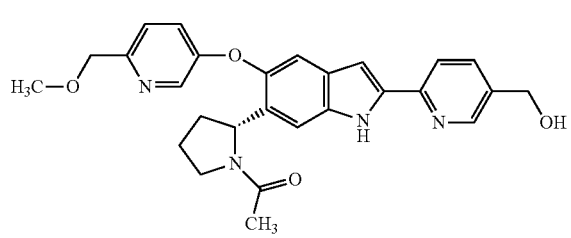

Synthesis of 6-[(R)-1-acetylpyrrolidin-2-yl]-2-(5-hydroxymethylpyridin-2-yl)-5-(6-methoxymethylpyridin-3-yloxy)-1H-indole The title compound (42 mg) was obtained as a pale yellow noncrystal solid by the same method as in Example 1, a method similar thereto, or combinations of them and usual methods, using 6-methoxymethylpyridin-3-ol instead of 6-(methylsulfonyl)-3-pyridinol.

The analytical data of the title compound are shown below.
1H-NMR (CDCl3) δ: 1.23-1.36 (1H, s), 1.64-1.93 (5H, m), 2.18-2.31 (1H, m), 3.41-3.56 (5H, m), 3.93-4.35 (2H, m), 4.54-4.58 (2H, m), 4.66-4.81 (2H, m), 5.11-5.16 (1H, m), 6.66-6.73 (1H, m), 6.91-7.00 (1H, m), 7.18 (1H, s), 7.20-7.30 (1H, m), 7.33-7.37 (1H, m), 7.87-7.92 (1H, m), 7.94-8.00 (1H, m), 8.36-8.38 (1H, m), 8.61 (1H, s).
ESI-MS (m/e): 473 [M+H]+

Example 16

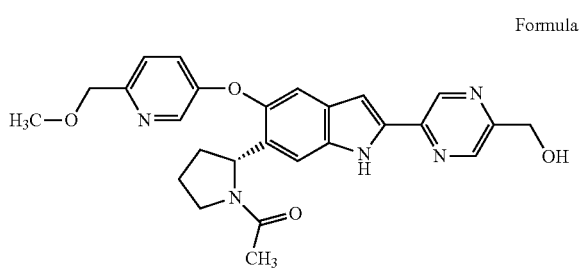 [SMILES: COCc1ccc(Oc2cc3cc(-c4ccc(CO)cn4)[nH]c3cc2[C@H]2CCCN2C(C)=O)cn1]

Synthesis of 6-[(R)-1-acetylpyrrolidin-2-yl]-2-(5-hydroxymethylpyrazin-2-yl)-5-(6-methoxymethylpyridin-3-yloxy)-1H-indole The title compound (18 mg) was obtained as a pale yellow noncrystal solid by the same method as in Example 1, a method similar thereto, or combinations of them and usual methods, using 6-methoxymethylpyridin-3-ol instead of 6-(methylsulfonyl)-3-pyridinol and 2-ethynyl-5-hydroxymethylpyrazine instead of (6-ethynylpyridin-3-yl)methanol.

The analytical data of the title compound are shown below.
1H-NMR (CDCl3) δ: 1.24-1.30 (1H, m), 1.83-2.16 (5H, m), 2.27-2.41 (1H, m), 2.96-3.08 (2H, m), 3.50 (3H, s), 3.64-3.89 (2H, m), 4.58 (2H, s), 4.88 (2H, d, J=5.6 Hz), 5.20-5.24 (1H, m), 7.04 (1H, s), 7.16-7.40 (4H, m), 8.39 (1H, d, J=2.7 Hz), 8.60 (1H, br-s), 9.00 (1H, br-s).
ESI-MS (m/e): 474 [M+H]+

Example 17

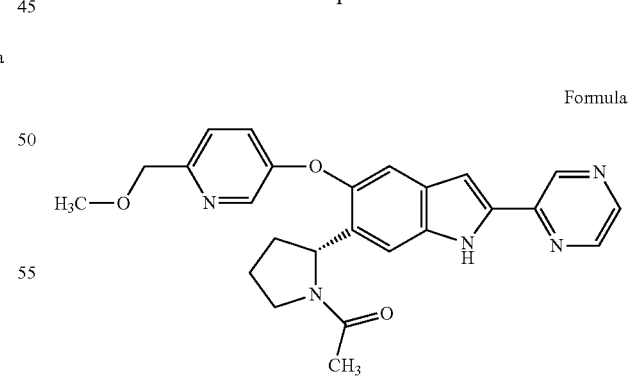

Synthesis of 6-[(R)-1-acetylpyrrolidin-2-yl]-5-(6-methoxymethylpyridin-3-yloxy)-2-(pyrazin-2-yl)-1H-indole The title compound (30 mg) was obtained as a pale yellow noncrystal solid by the same method as in Example 1, a method similar thereto, or combinations of them and usual methods, using 6-methoxymethylpyridin-3-ol instead of 6-(methylsulfonyl)-3-pyridinol and 2-ethynyl-pyrazine instead of (6-ethynylpyridin-3-yl)methanol.

The analytical data of the title compound are shown below.

1H-NMR (CDCl3) δ: 1.26 (1H, s), 1.84-2.07 (5H, m), 2.25-2.41 (1H, m), 3.50 (3H, s), 3.63-3.89 (2H, m), 4.58 (2H, s), 5.22 (1H, d, J=8.0 Hz), 7.03-7.05 (1H, m), 7.16-7.40 (3H, m), 8.38-8.41 (1H, m), 8.43-8.45 (1H, m), 8.53-8.55 (1H, m), 9.06-9.05 (1H, m), 9.43 (1H, s).

ESI-MS (m/e): 444 [M+H]+

Example 18

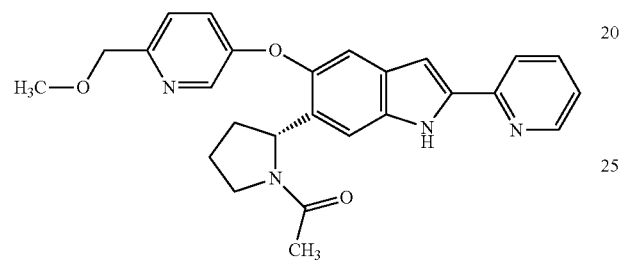

Formula

Synthesis of 6-[(R)-1-acetylpyrrolidin-2-yl]-5-(6-methoxymethylpyridin-3-yloxy)-2-(pyridin-2-yl)-1H-indole The title compound (35 mg) was obtained as a pale yellow noncrystal solid by the same method as in Example 1, a method similar thereto, or combinations of them and usual methods, using 6-methoxymethylpyridin-3-ol instead of 6-(methylsulfonyl)-3-pyridinol and 2-ethynyl-pyridin instead of (6-ethynylpyridin-3-yl)methanol.

The analytical data of the title compound are shown below.

1H-NMR (CDCl3) δ: 1.26 (1H, s), 1.85-2.04 (7H, m), 2.28-2.40 (1H, m), 3.49 (3H, s), 3.64-3.90 (2H, m), 4.57 (2H, s), 5.18-5.22 (1H, m), 6.90-6.92 (1H, m), 7.12-7.42 (4H, m), 7.67-7.80 (2H, m), 8.40 (1H, d, J=2.7 Hz), 8.58-8.61 (1H, m), 9.54-9.61 (1H, m).

ESI-MS (m/e): 443 [M+H]+

Example 19

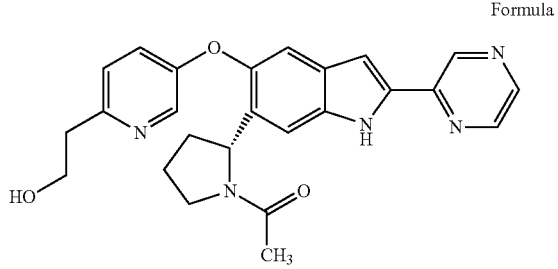 [SMILES: CC(=O)N1CCC[C@@H]1c1cc2[nH]c(-c3cnccn3)cc2cc1Oc1ccc(CCO)nc1]

Formula

Synthesis of 6-[(R)-1-acetylpyrrolidin-2-yl]-5-[6-(2-hydroxyethyl)pyridin-3-yloxy]-2-(pyrazin-2-yl)-1H-indole The title compound (37 mg) was obtained as a pale yellow noncrystal solid by the same method as in Example 1, a method similar thereto, or combinations of them and usual methods, using 6-(2-triisopropylsiloxyethyl)pyridin-3-ol instead of 6-(methylsulfonyl)-3-pyridinol and 2-ethynyl-pyrazine instead of (6-ethynylpyridin-3-yl)methanol.

The analytical data of the title compound are shown below.

1H-NMR (CDCl3) δ: 1.63 (2H, s), 1.91 (1H, s), 1.92 (3H, m), 2.32 (1H, m), 3.01 (2H, s), 3.86 (2H, m), 4.02 (2H, s), 5.23 (1H, m), 7.19 (4H, m), 8.52 (3H, m), 9.06 (1H, m), 9.43 (1H, m).

ESI-MS (m/e): 444 [M+H]+

Example 20

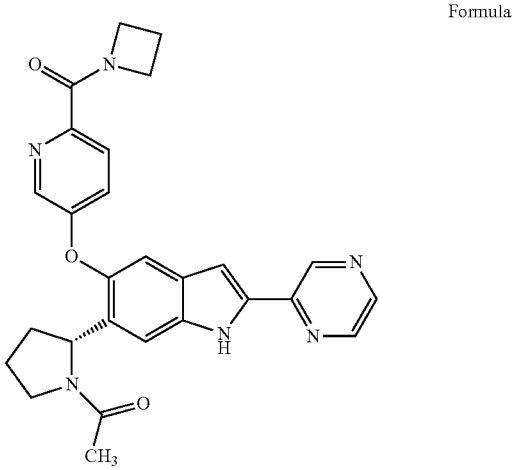 [SMILES: CC(=O)N1CCC[C@@H]1c1cc2[nH]c(-c3cnccn3)cc2cc1Oc1ccc(C(=O)N2CCC2)nc1]

Formula

Synthesis of 6-[(R)-1-acetylpyrrolidin-2-yl]-5-[6-(azetidin-1-ylcarbonyl)pyridin-3-yloxy]-2-(pyrazin-2-yl)-1H-indole The title compound (75 mg) was obtained as a pale brown solid by the same method as in Example 1, a method similar thereto, or combinations of them and usual methods, using 6-(azetidin-1-ylcarbonyl)pyridin-3-ol instead of 6-(methylsulfonyl)-3-pyridinol and 2-ethynyl-pyrazine instead of (6-ethynylpyridin-3-yl)methanol.

The analytical data of the title compound are shown below.

1H-NMR (CDCl3) δ: 1.69-2.43 (9H, m), 3.44-3.91 (2H, m), 4.17-4.28 (2H, m), 4.61-4.75 (2H, m), 5.09-5.37 (1H, m), 6.97-7.10 (1H, m), 7.14-7.37 (3H, m), 7.99-8.14 (1H, m), 8.30-8.56 (3H, m), 8.96-9.11 (1H, m), 9.45-9.95 (1H, m).

ESI-MS (m/e): 483 [M+H]+

Example 21

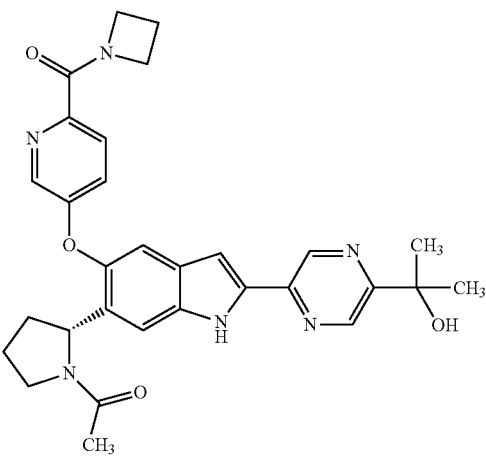

Synthesis of 6-[(R)-1-acetylpyrrolidin-2-yl]-5-[6-(azetidin-1-ylcarbonyl)pyridin-3-yloxy]-2-[5-(1,1-dimethylhydroxymethyl)pyrazin-2-yl]-1H-indole The title compound (78.5 mg) was obtained as a pale brown solid by the same method as in Example 1, a method similar thereto, or combinations of them and usual methods, using 6-(azetidin-1-ylcarbonyl)pyridin-3-ol instead of 6-(methylsulfonyl)-3-pyridinol and 2-(6-ethynylpyrazin-3-yl)propan-2-ol instead of (6-ethynylpyridin-3-yl)methanol.

The analytical data of the title compound are shown below.

1H-NMR (CDCl3) δ: 1.59-1.64 (6H, m), 1.78-2.08 (6H, m), 2.19-2.39 (3H, m), 3.42-3.81 (2H, m), 4.01-4.12 (1H, m), 4.17-4.25 (2H, m), 4.60-4.72 (2H, m), 5.08-5.30 (1H, m), 6.95-7.05 (1H, m), 7.14-7.21 (1H, m), 7.22-7.29 (2H, m), 7.94-8.09 (1H, m), 8.30-8.34 (1H, m), 8.69-8.77 (1H, m), 8.90-8.96 (1H, m), 9.97-10.34 (1H, m).

ESI-MS (m/e): 541 [M+H]+

Example 22

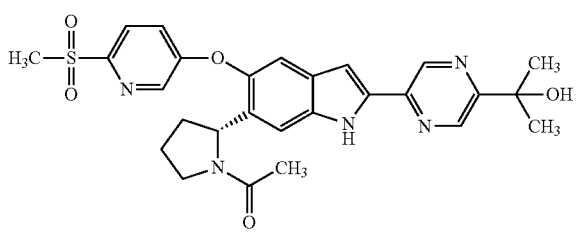

Synthesis of 6-[(R)-1-acetylpyrrolidin-2-yl]-2-[5-(1,1-dimethylhydroxymethyl)pyrazin-2-yl]-5-(6-methylsulfonylpyridin-3-yloxy)-1H-indole The title compound (140 mg) was obtained as a pale yellow noncrystal solid by the same method as in Example 1, a method similar thereto, or combinations of them and usual methods, using 2-(6-ethynylpyrazin-3-yl)propan-2-ol instead of (6-ethynylpyridin-3-yl)methanol.

The analytical data of the title compound are shown below.

1H-NMR (CD3OD) δ: 1.23 (1H, s), 1.60 (6H, s), 1.84 (1H, s), 2.00 (3H, m), 2.11 (1H, s), 2.37 (1H, m), 3.22 (1.5H, s), 3.24 (1.5H, s), 3.67 (1H, m), 3.82 (1H, m), 5.23 (1H, m), 7.19 (0.5H, s), 7.23 (0.5H, s), 7.38 (1.5H, m), 7.43 (0.5H, s), 7.58 (1H, m), 8.07 (1H, m), 8.57 (1H, m), 8.94 (1H, m), 9.01 (1H, m).

ESI-MS (m/e): 536 [M+H]+

Example 23

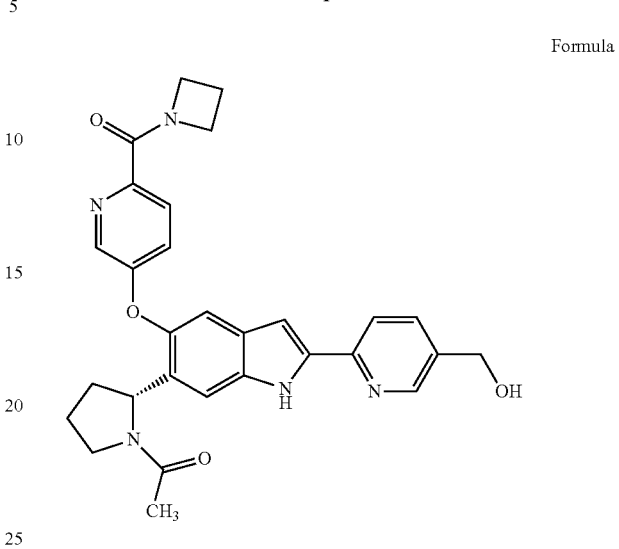

Synthesis of 6-[(R)-1-acetylpyrrolidin-2-yl]-5-[6-(azetidin-1-ylcarbonyl)pyridin-3-yloxy]-2-(5-hydroxymethylpyridin-2-yl)-1H-indole The title compound (12.3 mg) was obtained as a yellowish-brown solid by the same method as in Example 1, a method similar thereto, or combinations of them and usual methods, using 6-(azetidin-1-ylcarbonyl)pyridin-3-ol instead of 6-(methylsulfonyl)-3-pyridinol.

The analytical data of the title compound are shown below.

1H-NMR (DMSO-d6) δ: 1.61-1.90 (3H, m), 1.63 (1.5H, s), 1.87 (1.5H, s), 2.05-2.29 (3H, m), 3.38-3.66 (2H, m), 3.96-4.03 (2H, m), 4.50 (4H, s), 4.99-5.07 (1H, m), 5.30 (1H, br-s), 6.98-7.05 (1H, m), 7.15-7.27 (2H, m), 7.30-7.36 (1H, m), 7.70-7.76 (1H, m), 7.83-7.89 (2H, m), 8.26-8.34 (1H, m), 8.45-8.53 (1H, m), 11.51-11.74 (1H, m).

ESI-MS (m/e): 512 [M+H]+

Example 24

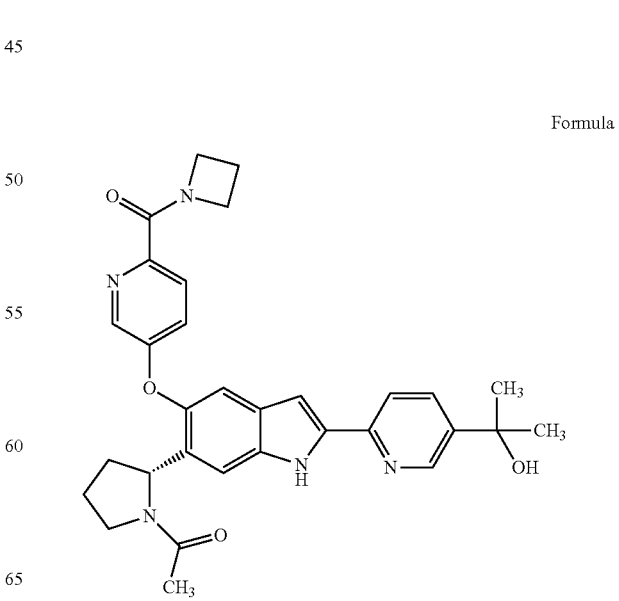

Synthesis of 6-[(R)-1-acetylpyrrolidin-2-yl]-5-[6-(azetidin-1-ylcarbonyl)pyridin-3-yloxy]-2-[5-(1,1-dimethylhydroxymethyl)pyridin-2-yl]-1H-indole The title compound (24.5 mg) was obtained as a yellow solid by the same method as in Example 1, a method similar thereto, or combinations of them and usual methods, using 6-(azetidin-1-ylcarbonyl)pyridin-3-ol instead of 6-(methylsulfonyl)-3-pyridinol and 2-(6-ethynylpyridin-3-yl)propan-2-ol instead of (6-ethynylpyridin-3-yl)methanol.

The analytical data of the title compound are shown below.

1H-NMR (DMSO-d6) δ: 1.43 (6H, s), 1.60-1.93 (6H, m), 2.06-2.28 (3H, m), 3.34-3.70 (2H, m), 3.97-4.03 (2H, m), 4.46-4.56 (2H, m), 4.95-5.29 (2H, m), 6.84-7.05 (1H, m), 7.15-7.28 (2H, m), 7.30-7.45 (1H, m), 7.72-7.92 (3H, m), 8.25-8.39 (1H, m), 8.42-8.71 (1H, m), 11.51-11.69 (1H, m).

ESI-MS (m/e): 540 [M+H]+

Example 25

Synthesis of 6-[(R)-1-acetylpyrrolidin-2-yl]-5-[6-(N,N-dimethylcarbamoyl)pyridin-3-yloxy]-2-(pyrazin-2-yl)-1H-indole The title compound (33 mg) was obtained as a yellow solid by the same method as in Example 1, a method similar thereto, or combinations of them and usual methods, using 6-methoxycarbonylpyridin-3-ol instead of 6-(methylsulfonyl)-3-pyridinol and 2-ethynyl-pyrazine instead of (6-ethynylpyridin-3-yl)methanol.

The analytical data of the title compound are shown below.

1H-NMR (DMSO-d6) δ: 1.63-1.96 (3H, m), 1.66 (1.5H, s), 1.90 (1.5H, s), 2.05-2.32 (1H, m), 2.93-2.97 (6H, m), 3.40-3.69 (2H, m), 5.02-5.16 (1H, m), 7.19-7.32 (3H, m), 7.33-7.39 (1H, m), 7.49-7.55 (1H, m), 8.28-8.32 (1H, m), 8.45-8.49 (1H, m), 8.58-8.64 (1H, m), 9.17-9.22 (1H, m), 11.67-11.89 (1H, m).

ESI-MS (m/e): 471 [M+H]+

Example 26

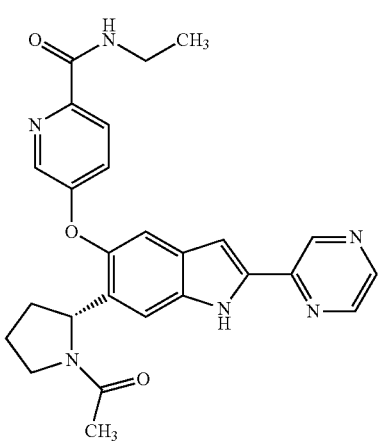

Formula

Synthesis of 6-[(R)-1-acetylpyrrolidin-2-yl]-5-[6-(N-ethylcarbamoyl)pyridin-3-yloxy]-2-(pyrazin-2-yl)-1H-indole The title compound (1.9 mg) was obtained as a yellow solid by the same method as in Example 1, a method similar thereto, or combinations of them and usual methods, using 6-methoxycarbonylpyridin-3-ol instead of 6-(methylsulfonyl)-3-pyridinol and 2-ethynyl-pyrazine instead of (6-ethynylpyridin-3-yl)methanol.

The analytical data of the title compound are shown below.

1H-NMR (DMSO-d6) δ: 1.06 (3H, t, J=7.0 Hz), 1.63-1.95 (3H, m), 1.66 (1.5H, s), 1.90 (1.5H, s), 2.09-2.30 (1H, m), 3.15-3.70 (4.0H, m), 5.01-5.13 (1H, m), 7.19-7.42 (4H, m), 7.91-7.97 (1H, m), 8.32-8.39 (1H, m), 8.45-8.51 (1H, m), 8.59-8.66 (2H, m), 9.17-9.24 (1H, m), 11.75-11.92 (1H, m).

ESI-MS (m/e): 471 [M+H]+

Example 27

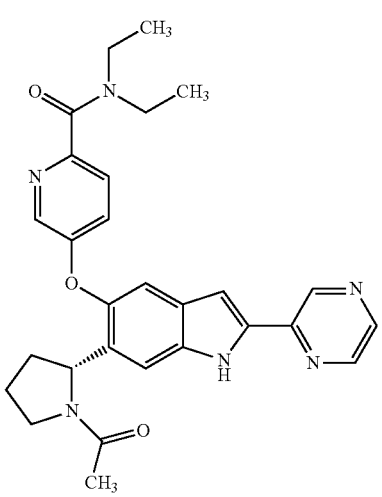

Formula

Synthesis of 6-[(R)-1-acetylpyrrolidin-2-yl]-5-[6-(N, N-dimethylcarbamoyl)pyridin-3-yloxy]-2-(pyrazin-2-yl)-1H-indole The title compound (22.5 mg) was obtained as a yellow solid by the same method as in Example 1, a method similar thereto, or combinations of them and usual methods, using 6-methoxycarbonylpyridin-3-ol instead of 6-(methylsulfonyl)-3-pyridinol and 2-ethynyl-pyrazine instead of (6-ethynylpyridin-3-yl)methanol.

The analytical data of the title compound are shown below.
1H-NMR (DMSO-d6) δ: 1.00-1.15 (6H, m), 1.63-1.95 (3H, m), 1.65 (1.5H, s), 1.90 (1.5H, s), 2.08-2.31 (1H, m), 3.19-3.69 (6H, m), 5.04-5.12 (1H, m), 7.19-7.39 (4H, m), 7.47-7.52 (1H, m), 8.26-8.31 (1H, m), 8.45-8.50 (1H, m), 8.60-8.63 (1H, m), 9.18-9.23 (1H, m), 11.70-11.87 (1H, m).
ESI-MS (m/e): 499 [M+H]+

Example 28

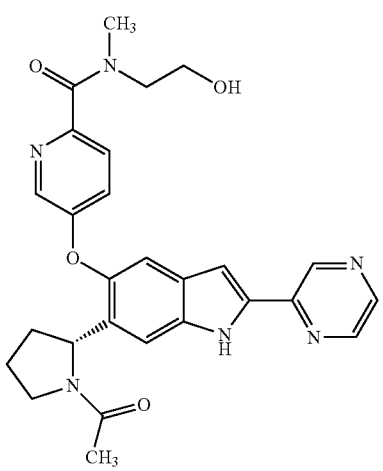

Formula

Synthesis of 6-[(R)-1-acetylpyrrolidin-2-yl]-5-{6-[N-(2-hydroxyethyl)]-N-methylcarbamoyl]pyridin-3-yloxy}-2-(pyrazin-2-yl)-1H-indole The title compound (14.9 mg) was obtained as a yellow solid by the same method as in Example 1, a method similar thereto, or combinations of them and usual methods, using 6-methoxycarbonylpyridin-3-ol instead of 6-(methylsulfonyl)-3-pyridinol and 2-ethynyl-pyrazine instead of (6-ethynylpyridin-3-yl)methanol.

The analytical data of the title compound are shown below.
1H-NMR (DMSO-d6) δ: 1.63-1.95 (3H, m), 1.65 (1.5H, s), 1.91 (1.5H, s), 2.08-2.31 (1H, m), 2.95 (1.5H, s), 2.99 (1.5H, s), 3.17-3.72 (6H, m), 4.73 (1H, br-s), 5.04-5.12 (1H, m), 7.19-7.41 (4H, m), 7.47-7.54 (1H, m), 8.24-8.33 (1H, m), 8.46-8.49 (1H, m), 8.60-8.64 (1H, m), 9.19-9.22 (1H, m), 11.74-11.93 (1H, m).
ESI-MS (m/e): 501 [M+H]+

INDUSTRIAL APPLICABILITY

An acetyl pyrrolidinyl indole derivative according to the present invention presented in Formula (I) or a pharmaceutically acceptable salt thereof is useful in treatment and/or prevention of diabetes mellitus, diabetes mellitus complications or obesity in the pharmaceutical field because of exhibiting an excellent glucokinase-activating effect.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

The invention claimed is:

1. A compound, or a pharmaceutically acceptable salt thereof, presented in Formula (I):

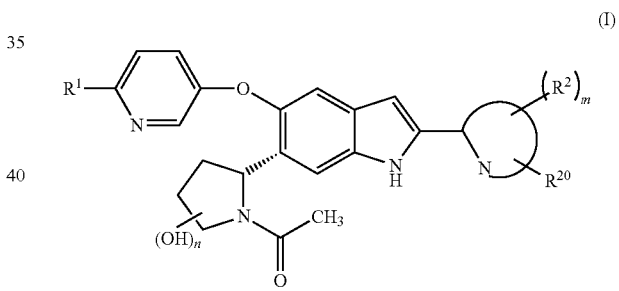

(I)

wherein $R^1$ represents a group selected from the group consisting of: a lower alkylsulfonyl group; lower alkyl groups substituted with a hydroxy or lower alkoxy group; a lower alkoxy group substituted with a hydroxy group; and a group of Formula (II):

(II)

wherein $R^3$ and $R^4$ independently represent a hydrogen atom or a lower alkyl group optionally substituted with a hydroxy group, or $R^3$ and $R^4$ together with a nitrogen atom to which they are attached represent a four- to seven-membered nitrogen-containing aliphatic ring;

$R^2$ represents a hydrogen atom;

$R^{20}$ is a branched lower alkyl group substituted with a hydroxy group or a group of Formula (III):

$$\underset{R^6}{\overset{O}{\underset{\|}{\text{—C—N}}}}\overset{R^5}{\underset{}{}}\qquad(III)$$

wherein $R^5$ and $R^6$ independently represent a hydrogen atom, or a lower alkyl group, or $R^5$ and $R^6$ together with a nitrogen atom to which they are attached represent a four- to seven-membered nitrogen-containing aliphatic ring;
m represents an integer of from 1 to 3;
n represents zero or 1; and
Formula (IV):

$$\text{(IV)}$$

represents a heteroaryl group selected from the group consisting of: pyridinyl, pyrazinyl, and pyrazolyl.

2. The compound of claim 1 or a pharmaceutically acceptable salt thereof, wherein n represents zero.

3. The compound of claim 1 or a pharmaceutically acceptable salt thereof, wherein $R^{20}$ represents a branched lower alkyl group substituted with a hydroxy group.

4. The compound of claim 1 or a pharmaceutically acceptable salt thereof, wherein $R^{20}$ is a group of Formula (III):

$$\underset{R^6}{\overset{O}{\underset{\|}{\text{—C—N}}}}\overset{R^5}{\underset{}{}}\qquad(III)$$

wherein $R^5$ and $R^6$ independently represent a hydrogen atom, or a lower alkyl group, or $R^5$ and $R^6$ together with a nitrogen atom to which they are attached represent a four- to seven-membered nitrogen-containing aliphatic ring.

5. The compound of claim 1 or a pharmaceutically acceptable salt thereof, wherein $R^1$ represents a lower alkylsulfonyl group.

6. The compound of claim 1 or a pharmaceutically acceptable salt thereof, wherein the group represented by Formula (IV) is:

(IV-1)

wherein shows a site attached to an indole ring.

7. The compound of claim 1 or a pharmaceutically acceptable salt thereof, selected from the group consisting of:

6-[(R)-1-acetylpyrrolidin-2-yl]-2-[5-(N-methylcarbamoyl)pyridin-2-yl]-5-(6-methylsulfonylpyridin-3-yloxy)-1H-indole, 6-[(R)-1-acetylpyrrolidin-2-yl]-2-[5-(1,1-dimethylhydroxymethyl)pyridin-2-yl]-5-(6-hydroxymethylpyridin-3-yloxy)-1H-indole, 6-[(R)-1-acetylpyrrolidin-2-yl]-2-[5-(1,1-dimethylhydroxymethyl)pyridin-2-yl]-5-(6-methylsulfonylpyridin-3-yloxy)-1H-indole, 6-[(R)-1-acetylpyrrolidin-2-yl]-5-[6-(azetidin-1-ylcarbonyl)pyridin-3-yloxy]-2-[5-(1,1-dimethylhydroxymethyl)pyrazin-2-yl]-1H-indole, 6-[(R)-1-acetylpyrrolidin-2-yl]-2-[5-(1,1-dimethylhydroxymethyl)pyrazin-2-yl]-5-(6-methylsulfonylpyridin-3-yloxy)-1H-indole, and 6-[(R)-1-acetylpyrrolidin-2-yl]-5-[6-(azetidin-1-ylcarbonyl)pyridin-3-yloxy]-2-[5-(1,1-dimethylhydroxymethyl)pyridin-2-yl]-1H-indole.

8. A pharmaceutical composition comprising a compound of claim 1, or a pharmaceutically acceptable salt thereof, in combination with a pharmaceutically acceptable carrier.

9. A method of treating type 2 diabetes in a mammalian patient in need of such treatment, comprising administering to the patient a compound of claim 1, or a pharmaceutically acceptable salt thereof, in an amount effective to treat type 2 diabetes.

10. A compound, or a pharmaceutically acceptable salt thereof, presented in Formula (I):

(I)

wherein $R^1$ is a lower alkoxy group substituted with a hydroxy group or a group of Formula (II):

(II)

wherein $R^3$ and $R^4$ each represent a lower alkyl group optionally substituted with a hydroxy group, or $R^3$ and $R^4$ together with a nitrogen atom to which they are attached represent a four- to seven-membered nitrogen-containing aliphatic ring;

$R^2$ represents a hydrogen atom;

$R^{20}$ independently represents a group selected from the group consisting of: hydrogen atoms, lower alkyl groups optionally substituted with hydroxy groups, lower alkoxy groups, and groups of Formula (III):

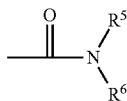 (III)

wherein R⁵ and R⁶ independently represent a hydrogen atom, or a lower alkyl group, or R⁵ and R⁶ together with a nitrogen atom to which they are attached represent a four- to seven-membered nitrogen-containing aliphatic ring;
m represents an integer of from 1 to 3;
n represents zero or 1; and
Formula (IV):

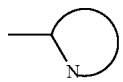 (IV)

represents a heteroaryl group selected from the group consisting of: pyridinyl, pyrazinyl, and pyrazolyl.

11. The compound of claim 10 or a pharmaceutically acceptable salt thereof, wherein R¹ is a lower alkoxy group substituted with a hydroxy group.

12. The compound of claim 10 or a pharmaceutically acceptable salt thereof, wherein R¹ is a group of Formula (II):

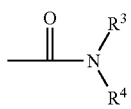 (II)

wherein R³ and R⁴ each represent a lower alkyl group optionally substituted with a hydroxy group.

13. The compound of claim 10 or a pharmaceutically acceptable salt thereof, wherein R¹ is a group of Formula (II):

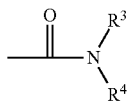 (II)

wherein R³ and R⁴ together with a nitrogen atom to which they are attached represent a four- to seven-membered nitrogen-containing aliphatic ring.

14. The compound of claim 10 or a pharmaceutically acceptable salt thereof, wherein n represents zero.

15. The compound of claim 10 or a pharmaceutically acceptable salt thereof, wherein the group represented by Formula (IV):

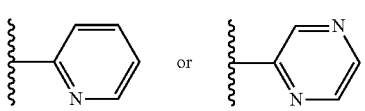 (IV-1)

wherein

shows a site attached to an indole ring.

16. The compound of claim 10 or a pharmaceutically acceptable salt thereof, selected from the group consisting of:
  6-[(R)-1-acetylpyrrolidin-2-yl]-5-[6-(2-hydroxyethoxy)pyridin-3-yloxy]-2-(pyridin-2-yl)-1H-indole,
  6-[(R)-1-acetylpyrrolidin-2-yl]-5-[6-(2-hydroxyethoxy)pyridin-3-yloxy]-2-(pyrazin-2-yl)-1H-indole,
  6-[(R)-1-acetylpyrrolidin-2-yl]-5-[6-(2-hydroxyethoxy)pyridin-3-yloxy]-2-(5-methylpyrazin-2-yl)-1H-indole,
  6-[(R)-1-acetylpyrrolidin-2-yl]-5-[6-(2-hydroxyethoxy)pyridin-3-yloxy]-2-(5-hydroxymethylpyrazin-2-yl)-1H-indole,
  6-[(R)-1-acetylpyrrolidin-2-yl]-5-[6-(azetidin-1-ylcarbonyl)pyridin-3-yloxy]-2-(pyrazin-2-yl)-1H-indole,
  6-[(R)-1-acetylpyrrolidin-2-yl]-5-[6-(azetidin-1-ylcarbonyl)pyridin-3-yloxy]-2-[5-(1,1-dimethylhydroxymethyl)pyrazin-2-yl]-1H-indole,
  6-[(R)-1-acetylpyrrolidin-2-yl]-5-[6-(azetidin-1-ylcarbonyl)pyridin-3-yloxy]-2-(5-hydroxymethylpyridin-2-yl)-1H-indole,
  6-[(R)-1-acetylpyrrolidin-2-yl]-5-[6-(azetidin-1-ylcarbonyl)pyridin-3-yloxy]-2-[5-(1,1-dimethylhydroxymethyl)pyridin-2-yl]-1H-indole; and
  6-[(R)-1-acetylpyrrolidin-2-yl]-5-{6-[N-(2-hydroxyethyl)]-N-methylcarbamoyl]pyridin-3-yloxy}-2-(pyrazin-2-yl)-1H-indole.

17. A pharmaceutical composition comprising a compound of claim 10, or a pharmaceutically acceptable salt thereof, in combination with a pharmaceutically acceptable carrier.

18. A method of treating type 2 diabetes in a mammalian patient in need of such treatment, comprising administering to the patient a compound of claim 10, or a pharmaceutically acceptable salt thereof, in an amount effective to treat type 2 diabetes.

* * * * *

UNITED STATES PATENT AND TRADEMARK OFFICE
CERTIFICATE OF CORRECTION

PATENT NO.        : 8,592,428 B2                                                      Page 1 of 1
APPLICATION NO. : 13/058626
DATED             : November 26, 2013
INVENTOR(S)       : Imamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
Twenty-second Day of September, 2015

Michelle K. Lee
*Director of the United States Patent and Trademark Office*